US011931556B2

(12) United States Patent
Jakobsen et al.

(10) Patent No.: US 11,931,556 B2
(45) Date of Patent: Mar. 19, 2024

(54) DRUG INJECTION DEVICE WITH DEFLECTABLE TRANSDUCER

(71) Applicant: Novo Nordisk A/S, Bagsvaerd (DK)

(72) Inventors: Nikolaj Eusebius Jakobsen, Soeborg (DK); Per Einar Pontus Holm, Malmoe (SE)

(73) Assignee: Novo Nordisk A/S, Bagsvaerd (DK)

( * ) Notice: Subject to any disclaimer, the term of this patent is extended or adjusted under 35 U.S.C. 154(b) by 899 days.

(21) Appl. No.: 16/966,562

(22) PCT Filed: Feb. 2, 2019

(86) PCT No.: PCT/EP2019/052559
§ 371 (c)(1),
(2) Date: Jul. 31, 2020

(87) PCT Pub. No.: WO2019/149918
PCT Pub. Date: Aug. 8, 2019

(65) Prior Publication Data
US 2020/0360616 A1    Nov. 19, 2020

(30) Foreign Application Priority Data

Feb. 2, 2018  (EP) .................................... 18155015

(51) Int. Cl.
*A61M 5/315* (2006.01)
*G01F 11/02* (2006.01)
(Continued)

(52) U.S. Cl.
CPC .... *A61M 5/31553* (2013.01); *A61M 5/31556* (2013.01); *G01F 11/029* (2013.01);
(Continued)

(58) Field of Classification Search
CPC .......... A61M 5/31553; A61M 2205/52; A61M 2205/33; A61M 2205/3592; A61M 5/31568
See application file for complete search history.

(56) References Cited

U.S. PATENT DOCUMENTS

| 4,379,245 A | 4/1983 | Goldstein |
| 4,853,580 A | 8/1989 | Sula |

(Continued)

FOREIGN PATENT DOCUMENTS

| CN | 101727540 A | 6/2010 |
| EP | 1182118 A2 | 2/2002 |

(Continued)

*Primary Examiner* — Robert J Utama
*Assistant Examiner* — Neeraja Gollamudi
(74) *Attorney, Agent, or Firm* — Wesley Nicolas

(57) ABSTRACT

The present invention provides a drug injection device (100, 100', 100") comprising a first element (130) and a second element (102, 102', 102") configured to undergo movement relative to each other corresponding to an action performed on or by the drug injection device (100, 100', 100"), wherein the first element (130) comprises serially disposed protrusions (133), and wherein the second element (102, 102', 102") comprises a second element base and a deflectable transducer (170, 170', 170"). The deflectable transducer (170, 170', 170") defines a base portion attached to the second element base, and a deflectable portion (162) configured for sequentially cooperating with the plurality of protrusions (133), wherein a processor (165) is electrically connected with the deflectable transducer (170, 170', 170") to register activation signals. The deflectable transducer (170, 170', 170") comprises a carrier foil (161) that extends from the base portion to the tip end of the deflectable portion (162), and a sensor element comprising a strain sensitive material (175) disposed on the carrier foil (161) and extending from the base portion towards the tip end of the (Continued)

deflectable portion (162), wherein the carrier foil (161), between the base portion and tip end of the deflectable portion (162), comprises a non-supported portion having said strain sensitive material (175) disposed at least partly along the non-supported portion.

20 Claims, 10 Drawing Sheets

(51) Int. Cl.
  *H02N 2/18* (2006.01)
  *H10N 30/30* (2023.01)
(52) U.S. Cl.
  CPC . *A61M 2205/0294* (2013.01); *A61M 2205/33* (2013.01); *A61M 2205/3584* (2013.01); *A61M 2205/52* (2013.01); *A61M 2205/8206* (2013.01); *H02N 2/18* (2013.01); *H10N 30/302* (2023.02)

(56) References Cited

U.S. PATENT DOCUMENTS

| | | |
|---|---|---|
| 5,034,648 A | 7/1991 | Gastgeb |
| 6,277,099 B1 * | 8/2001 | Strowe ............ A61M 5/3158 |
| | | 604/207 |
| 2005/0239162 A1 | 10/2005 | Verdini et al. |
| 2010/0145656 A1 | 6/2010 | Koehler et al. |
| 2012/0092182 A1 | 4/2012 | Daniel et al. |
| 2015/0033566 A1 | 2/2015 | Chen et al. |
| 2015/0302818 A1 | 10/2015 | Cowe et al. |

FOREIGN PATENT DOCUMENTS

| | | |
|---|---|---|
| KR | 20160024644 A | 3/2016 |
| WO | 03107523 A1 | 12/2003 |
| WO | 2014083343 | 6/2014 |
| WO | 2015071354 | 5/2015 |
| WO | 2018078178 | 5/2018 |
| WO | 2019046053 | 3/2019 |

* cited by examiner

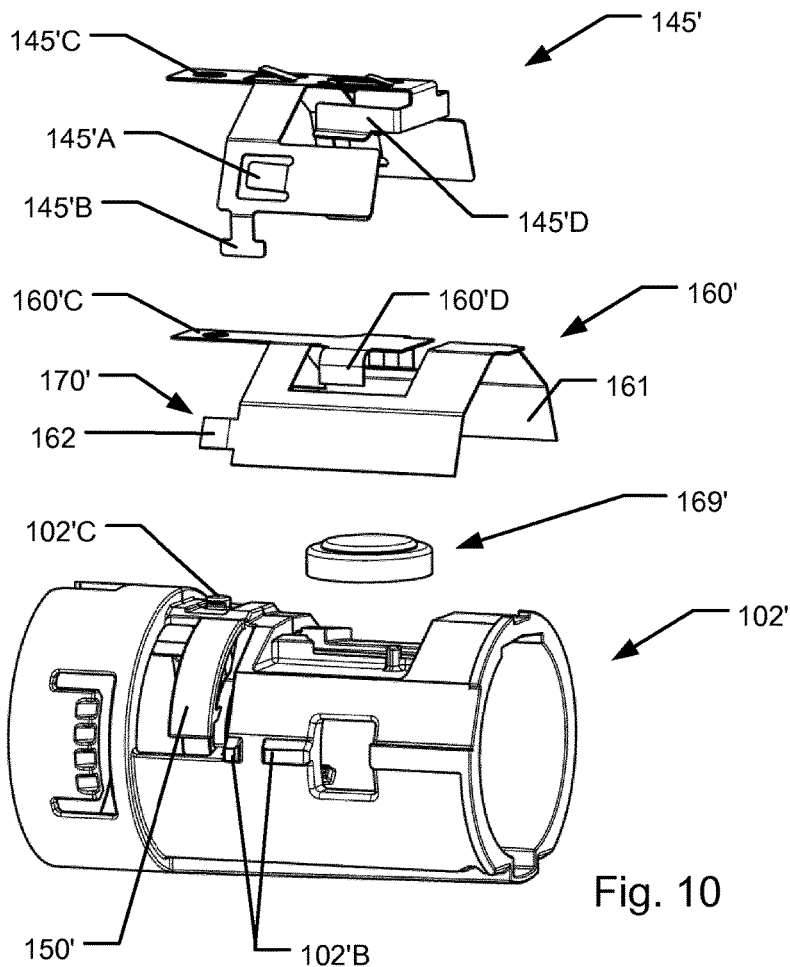
Fig. 10
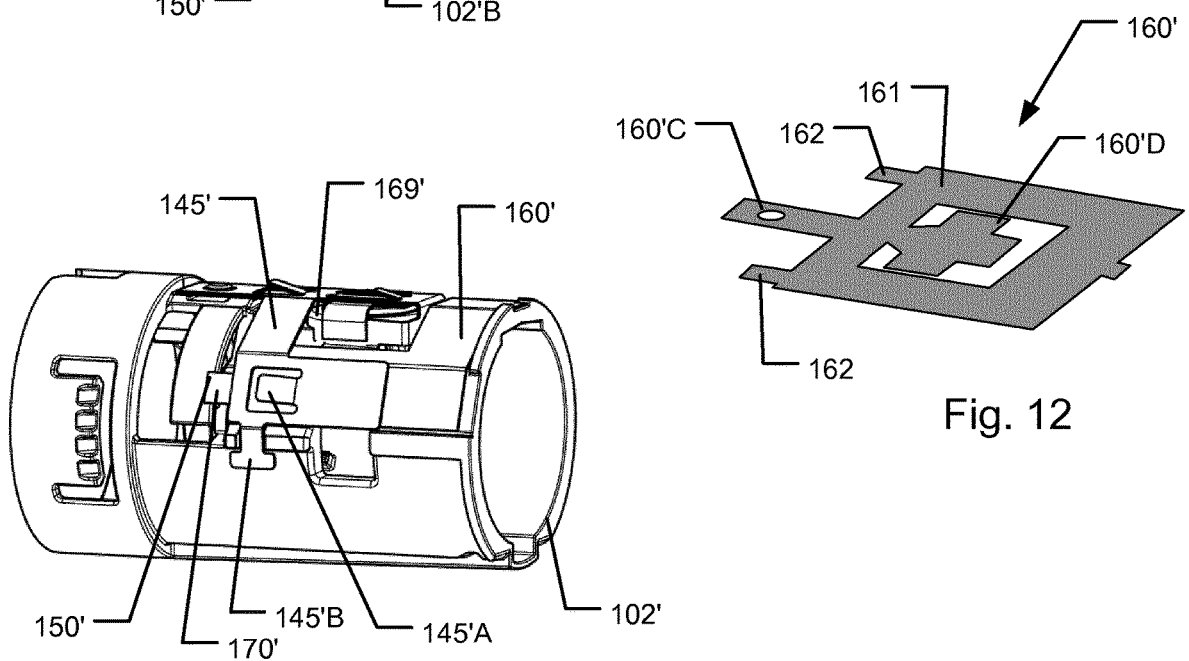
Fig. 11
Fig. 12

DRUG INJECTION DEVICE WITH DEFLECTABLE TRANSDUCER

CROSS-REFERENCE TO RELATED APPLICATIONS

This application is a 35 U.S.C. § 371 National Stage application of International Application PCT/EP2019/052559 (published as WO 2019/149918), filed Feb. 2, 2019, which claims priority to European Patent Application 18155015.3, filed Feb. 2, 2018; the contents of which are incorporated herein by reference.

FIELD OF THE INVENTION

The present invention relates generally to devices for delivering medicine to a subject, and more specifically to injection devices capable of expelling one or more doses of drug from a drug reservoir.

BACKGROUND OF THE INVENTION

In the diabetes care segment parenteral drug administration carried out using a traditional vial and syringe system is increasingly being substituted by administration using a pen injection device. Pen injection devices are particularly convenient in that they allow the user to perform a dosed injection from a prefilled drug reservoir without first having to manually transfer the particular dose from one reservoir (the vial) to another (the syringe).

Predominantly, two types of pen injection devices are available, durable injection devices being capable of delivering one or more doses of drug from a prefilled drug cartridge which can be loaded into the device before use and replaced after exhaustion, and disposable injection devices being capable of delivering one or more doses of drug from a prefilled and non-exchangeable drug cartridge. Each of these types of pen injection devices are, or may in principle be, realised in various sub-types, such as e.g. single shot devices adapted to deliver only one dose from a drug cartridge, multi-shot devices capable of delivering a plurality of doses from a drug cartridge, manual devices, where the user provides the force needed for injection, automatic devices having a built-in energy source releasable to occasion the injection, fixed dose devices adapted to deliver a predetermined dose of drug, variable dose devices offering delivery of different doses of drug, settable by the user, etc.

As the labels suggest a durable injection device is intended for use over a considerable period of time during which multiple drug cartridges are exhausted and replaced, whereas a disposable injection device is intended for use until its dedicated drug cartridge is exhausted, after which the entire injection device is discarded.

In the treatment of diabetes it is advisable to keep a log of the administered doses of a particular drug (e.g. insulin or glp-1), as well as the respective times of dose administration. Some injection devices accordingly offer electronic dose capturing and the opportunity to review dose related information on a digital display.

As an example, U.S. Pat. No. 6,277,099 B1 (Becton, Dickinson and Company) discloses an electronic medication delivery pen, wherein a dialled dose is detected by a piezoelectric sensor arrangement, activated in response to rotation of a user manipulable dose knob, and displayed on a liquid crystal display. The medication delivery pen also comprises a memory function, which together with the liquid crystal display provides an operable interface for conveying the dose size and the time of the last five injections.

US 2015/0302818 A1 (Owen Mumford Limited) discloses the use of an electronic paper display device in addition to a conventional scale drum merely to enable dose display of a larger font size. The electronic display is driven by signals from piezoelectric elements which are successively energised during rotation of a dose setting knob.

Until recently, the use of electronic features like the ones above has been limited to durable injection devices, as the additional cost connected with an inclusion of such features in a disposable injection device has been considered to lead to an economically unviable end product. However, the advances within particularly printed electronics are promising vis-à-vis the possibility of producing disposable injection devices with integrated electronic components at a reasonable cost.

WO 2015/071354 A1 (Novo Nordisk A/S) discloses a drug delivery device having a flexible sheet mounted at least in part to the exterior of its housing, the flexible sheet carrying e.g. printed electronic components such as a display, a processor, an energy source, and input means actuatable by a an action performed on or by the device. The display is configured to visually indicate e.g. the size of a set dose, the size of an expelled dose, and/or a time parameter in response to actuation of the input means. The input means are exemplified by various switch structures, each adapted to provide connection to an interior device component through an opening in the housing.

Simple and affordable switch structures are generally prone to errors, for example faulty switch activations which are not representative for the movements of one or more components of the device. For example, due to electromagnetic noise, the signals from switches or sensors may generate unreliable signals.

SUMMARY OF THE INVENTION

It is an object of the invention to eliminate or reduce at least one drawback of the prior art, or to provide a useful alternative to prior art solutions.

In particular, it is an object of the invention to provide a drug injection device having means for enabling reliable and accurate monitoring of movements of one or more components of the device.

It is a further object of the invention to provide a drug injection device having means for electronic determination of a set and/or expelled dose of drug.

It is an even further object of the invention to provide such a drug injection device which is relatively simple and inexpensive to produce.

In the disclosure of the present invention, aspects and embodiments will be described which will address one or more of the above objects and/or which will address objects apparent from the following text.

In accordance with a first aspect, a drug injection device embodying the principles of the present invention comprises:

a first element and a second element configured to undergo relative movement in respect of each other, said movement corresponding to an action performed on or by the drug injection device and representing an amount of drug delivered or to be delivered from the drug injection device, wherein the first element comprises either a single protrusion, or a plurality of protrusions serially disposed along a trajectory of said relative movement, the protrusions protruding in a protruding direction, wherein the second element comprises one or more deflectable transducers, wherein the deflectable transducer(s) are configured for sequentially cooperating with the protrusion(s) of the first element to generate an activation signal as the deflectable transducer is deflected in the protruding direction when travelling past each protrusion, wherein each deflectable transducer defines a base portion attached to the second element, the base portion being non-movably arranged in the protruding direction, and further defines a deflectable portion having a tip end, wherein the deflectable portion deflects relative to the base portion in the protruding direction upon cooperation with protrusions of the first element, and a processor electrically connected with the one or more deflectable transducers to register generated activation signals, and configured to determine, from registered activation signals, an amount of drug delivered or to be delivered from the drug injection device, wherein each deflectable transducer is provided comprising:
a carrier foil that extends from the base portion to the tip end of the deflectable portion, and
a sensor element comprising a strain sensitive material disposed on the carrier foil and extending from the base portion towards the tip end of the deflectable portion, and wherein the carrier foil, between the base portion and tip end of the deflectable portion, comprises a non-supported portion having said strain sensitive material disposed at least partly along the non-supported portion.

By forming the carrier foil to be non-supported by other components, i.e. except for the strain sensitive material itself, the strain sensitive material disposed along the non-supported portion of the carrier foil is exclusively supported by the carrier foil. Due to the non-supported portion of the carrier foil, a high bending degree of the deflectable transducer at locations where the strain sensitive material is disposed can be obtained. As a result, superior signal amplitudes are obtainable which results in high signal to noise ratios to be obtained. Also, the improved signal amplitudes can be utilized for particular purposes such as waking up a dormant or sleeping micro-processor. Bending out the substrate itself and releasing it quickly gives a high voltage output, which is easily distinguished form noise in the system. The substrate forms a very thin and short beam and, therefore, it becomes less sensitive to vibrations in the injection device which may occur if the device is being unintentionally dropped on a hard surface.

In some embodiments, the carrier foil and the sensor element may be formed to form a cantilever structure having a free end disposed at the tip end of the deflectable portion.

In some embodiments of the deflectable transducer, the tip end of the deflectable portion defines a free end that is not fixedly attached to other components. This enables the free end of the deflectable transducer to become acted upon by the protrusions, such as directly by the protrusions of the first element, or alternatively by an activating intermediate deflectable structure arranged between the first element and the deflectable transducer. The free end of the deflectable transducer may be configured so as to be acted upon by the protrusions by an impinging action or by being deflected while continuous abutment is maintained.

In exemplary embodiments the non-supported portion of the carrier foil includes portions having a thickness (in the protruding direction) within 40-500 microns, such as a thickness within 50-250 microns, such as a thickness within 75-200 microns, or such as a thickness within 100-125 microns.

The carrier foil may exhibit a modulus of elasticity between 0.1-100 GPa, such as between 0.2-50 GPa, such as between 0.1-20 GPa, such as between 1-10 GPa.

The carrier foil may be a planar sheet-formed foil and may be provided as a single-layer foil or multi-layer foil. In some embodiments the carrier foil is provided as one or more layers which are made from non-metallic materials. In some embodiments the single-layer or multilayer carrier foil is made from a polymeric material, such as Polyethylene terephthalate (PET).

The deflectable portion of each deflectable transducer is configured to sequentially cooperate with the protrusions of the first element by directly engaging the protrusions of the first element. In alternative embodiments of a drug injection device wherein the first element only includes a single protrusion rather than a plurality of protrusions, the deflectable transducer according to instant invention may be also be utilized.

In embodiments of drug injection devices which include a plurality of deflectable transducers, said plurality of deflectable transducers may be arranged in a manner such that they are offset with respect to each other along the trajectory of movement and so as to provide a phase shift between generated activation signals picked up by the individual deflectable transducers during relative movement.

Some embodiments of said injection device are configured so that said relative movement is provided as a unidirectional movement of the first element relative to the second element in a first direction, wherein the carrier foil for a respective deflectable transducer is arranged so that it comprises a first segment extending from the base portion generally counter to the first direction to a bending portion and further comprises a second segment extending in a direction generally in the first direction from the bending portion to the tip end of the deflectable portion so that the second segment includes sub-segments that form angles less than 80 degrees, preferable less than 60 degrees, and more preferably less than 40 degrees relative to the first segment, and wherein the non-supported portion of the carrier foil having said strain sensitive material disposed is arranged along the second segment.

By bending the deflectable transducer more than 130 degrees at the bending portion a pretension in the carrier foil is obtained. This helps getting a uniform and high amplitude signal, as the pretension forces the second segment containing the strain sensitive material down to the bottom between neighbouring protrusions. The geometry also ensures that the second segment of the carrier foil becomes deflected to a degree which is close to the entire height of the protrusions resulting in a superior voltage output. The pretension additionally takes up the tolerances in the system.

In certain embodiments, the strain sensitive material is additionally disposed at portions including the bending portion of the carrier foil. The strain sensitive material may be disposed on the side of the carrier foil that faces radially inwards, i.e. the side that faces inwards at the inner side of the bend.

In certain embodiments, the said angles are defined in a state where the respective deflectable transducer cooperates with the peak of a protrusion. In other embodiments, the said angles are defined in a state where the respective deflectable transducer is located in the valley formed between two neighbouring protrusions.

Exemplary embodiments may include embodiments wherein the bending portion defines a bended carrier foil having a radius of curvature at the bending portion within 0.1 mm and 1.0 mm, such as within 0.2 mm and 0.5 mm.

Some exemplary embodiments may be so configured so that each deflectable transducer sequentially cooperates with the protrusions of the first element by cooperating indirectly via a respective activation arm arranged between the first element and the deflectable transducer, wherein the activation arm comprises a base fixedly arranged relative to the second element and a deflectable end being configured to resiliently deflect in the protruding direction upon cooperation with the protrusions of the first element, and wherein the deflectable end of the carrier foil cooperates with the deflectable end of the activation arm by direct engagement with the activation arm.

In such embodiments, the non-supported portion of the carrier foil is arranged between the base portion and the location where the deflectable end of the carrier foil engages with the deflectable end of the activation arm.

In certain embodiments, the activation arm comprises a resiliently deflectable polymeric or metallic material portion configured to become deflected in the protruding direction upon cooperating with the protrusions of the protrusion configuration.

In some embodiments the deflectable end of the carrier foil is attached to a surface of the deflectable end of the activation arm. In other embodiments, the deflectable portion of the carrier foil is not attached to the deflectable end of the activation arm.

In further embodiments the non-supported portion of the carrier foil includes the tip end of the deflectable transducer.

In certain embodiments, a retaining member is arranged attaching the base portion of the deflectable transducer with the second element, the base portion of the deflectable transducer being clamped between the retaining element and the second element.

The retaining element may in some embodiments be formed to comprise a retaining portion configured to provide a spring force onto the base portion of the deflectable transducer for urging the base portion of the deflectable transducer into contact with the base of the activation arm. In particular embodiments, the retaining portion do not engage the deflectable end of the deflectable transducer.

In some embodiments the retaining member is formed from spring steel. In configurations that include a plurality of independent deflectable transducers, the retaining member may include additional retaining portions so that each retaining portion is configured to provide a spring force onto the base portion of a respective deflectable transducer to retain the transducer relative to the base of the activation arm.

In some exemplary embodiments, each of the protrusions may be so formed as to provide, upon said relative movement, a gradually rising deflection of the deflectable transducer into a biased state followed by an abrupt release from the biased state as each protrusion pass the deflectable transducer.

In particular embodiments, the said relative movement is a relative rotational movement around an axis, wherein the first element defines a cylindrical member arranged coaxially with the axis and wherein the protrusions of the protrusion configuration are regularly disposed on the first element around the axis. In some embodiments, the first element may be arranged to circumscribe the second element. Alternatively the second element may be arranged to circumscribe the first element. Still alternatively, the first and the second elements may be arranged axially in line with surfaces facing each other and with the protrusions of the first element pointing axially towards the second element.

In some configurations of drug injection devices, the drug injection device defines a ratchet mechanism between the first element and the second element so as to prevent relative movement between the first element and the second element in a direction counter to said relative movement. In other embodiments, the relative movement is configured reversible.

Each of the one or more deflectable transducers may be provided as, or may comprise one of a piezoelectric sensor, a piezoresistive sensor and a strain gauge.

In certain embodiments the one or more deflectable transducers comprise piezoelectric material formed onto the carrier foil by a printing process. Some embodiments contain only a single deflectable transducer. Other embodiments contain a plurality of individual deflectable transducers. Some embodiments comprise a plurality of individual deflectable transducers, wherein the individual deflectable transducers are formed on a carrier foil which is common to the plurality of deflectable transducers.

In some embodiments the one or more deflectable transducers is provided as a plurality of deflectable transducers that are formed on a carrier foil sheet which is common to the plurality of deflectable transducers, and wherein the processor may be disposed on the same carrier foil sheet as the deflectable transducers. Further electronic components may also be included on the same carrier foil sheet.

In accordance with a second aspect, a drug injection device embodying the principles of the present invention comprises:

a first element and a second element configured to undergo relative movement in respect of each other, said movement corresponding to an action performed on or by the drug injection device and representing an amount of drug delivered or to be delivered from the drug injection device, wherein the first element comprises either a single protrusion, or a plurality of protrusions serially disposed along a trajectory of said relative movement, the protrusions protruding in a protruding direction, wherein the second element comprises a second element base and at least one deflectable transducer configured for sequentially cooperating with the protrusion(s) of the first element to generate an activation signal as the deflectable transducer is deflected in the protruding direction when travelling past each protrusion, wherein the at least one deflectable transducer defines a base portion attached to the second element, the base portion being non-movably arranged in the protruding direction, and further defines a deflectable portion having a tip end, wherein the deflectable portion deflects relative to the base portion in the protruding direction upon cooperation with protrusion(s) of the first element, and a processor electrically connected with the one or more deflectable transducers to register generated activation signals, and configured to determine, from registered activation signals, an amount of drug delivered or to be delivered from the drug injection device, wherein the at least one deflectable transducer comprises:
a carrier foil that extends from the base portion to the tip end of the deflectable portion, and
a sensor element comprising a strain sensitive material disposed on the carrier foil and extending from the base portion towards the tip end of the deflectable portion, and wherein a retaining member is arranged to retain the base portion of the deflectable transducer relative to the second element, the base portion of the deflectable transducer being clamped between the retaining element and the second element.

By utilizing said retaining member to clamp the base portion of the deflectable transducer relative to the second element, such as relative to the second element base, the use of adhesives during production is avoided. This provides for an improved assembly procedure and further provides for a superior long-term stability of the sensor assembly. In addition, this enables selection of a greater variety of materials that can be used as carrier foil, and the second element, respectively. Hence, the risk of detachment of carrier foil from the second element is mitigated compared to alternative embodiments including a gluing or fusing process for attaching the carrier foil relative to the second element.

In further embodiments the retaining element comprises a retaining portion configured to provide a spring force onto the base portion of the deflectable transducer for urging the base portion into contact with the second element, e.g. the second element base.

In further embodiments, the second element comprises an activation arm, such a resilient deflectable arm to cooperate with the one or more protrusion(s) of the first element. In such embodiments the at least one deflectable transducer cooperates with the protrusion(s) of the first element, e.g. sequentially cooperates with a plurality of protrusions, by cooperating indirectly via a respective activation arm arranged between the first element and the deflectable transducer, wherein the activation arm comprises a base fixedly arranged relative to the second element, and a deflectable end being configured to resiliently deflect in the protruding direction upon cooperation with the protrusion(s) of the first element, and wherein the deflectable end of the carrier foil cooperates with the deflectable end of the activation arm by direct engagement with the activation arm. The retaining portion is in some embodiments configured for urging the base portion of the deflectable transducer into contact with the second element base, e.g. the base of the activation arm.

In particular embodiments, the deflectable portion of the carrier foil is not attached to the deflectable end of the activation arm, and may in some embodiments not be engaged by the retaining member.

In some embodiments the at least one deflectable transducers is provided as a plurality of deflectable transducers that are formed on a carrier foil sheet which is common to the plurality of deflectable transducers, and wherein the processor is disposed on the same carrier foil sheet as the deflectable transducers. Further electronic components, such as a power unit, may also in some embodiments be included on the same carrier foil sheet.

In further embodiments, the retaining member comprises a plurality of retaining portions each configured to provide a spring force onto the base portion of a respective one of the deflectable transducers for urging the base portion of the deflectable transducer into contact with the second element base, e.g. the base of the activation arm.

In still further embodiments, the retaining member comprises retaining structure for retaining a power unit, such as one or more batteries, relative to the second element. In such embodiments, the retaining structure may comprise retaining portions configured to urge electrode portions of the carrier foil sheet into electrical conductive contact with electrodes of the power unit. In particular forms of the retaining member, the retaining member defines a unitary member, e.g. made from a single piece of folded sheet steel, such as sheet steel prepared by a metal stamping process.

Further embodiments of the drug injection device in accordance with the second aspect include any of the further optional features mentioned above in connection with the drug injection device in accordance with the first aspect.

In particular embodiments the drug injection device according to the first or the second aspect defines a housing extending along a longitudinal axis, and further comprises a drug expelling mechanism for expelling a volume of drug from a reservoir. The first element and/or the second element form part of the drug expelling mechanism. Said relative movement is provided as a relative unidirectional movement between the first element and the second element about the longitudinal axis during a drug expelling action in accordance with an expelled dose.

As used herein the term "drug injection device" covers all types of devices for administering drug transcutaneously, i.e. including devices which are conventionally labelled injection devices (with or without an injection needle), where the drug is delivered over a relatively short time span, and devices which are conventionally labelled infusion devices, where the drug is delivered continuously over a longer period of time.

Also, as used herein, the terms "distal" and "proximal" denote positions at or directions along a drug delivery device, where "distal" refers to the drug outlet end and "proximal" refers to the end opposite the drug outlet end.

In the present specification, reference to a certain aspect or a certain embodiment (e.g. "an aspect", "a first aspect", "one embodiment", "an exemplary embodiment", or the like) signifies that a particular feature, structure, or characteristic described in connection with the respective aspect or embodiment is included in, or inherent of, at least that one aspect or embodiment of the invention, but not necessarily in/of all aspects or embodiments of the invention. It is emphasized, however, that any combination of the various features, structures and/or characteristics described in relation to the invention is encompassed by the invention unless expressly stated herein or clearly contradicted by context.

The use of any and all examples, or exemplary language (e.g., such as, etc.), in the text is intended to merely illuminate the invention and does not pose a limitation on the scope of the same, unless otherwise claimed. Further, no language or wording in the specification should be construed as indicating any non-claimed element as essential to the practice of the invention.

BRIEF DESCRIPTION OF THE DRAWINGS

In the following the invention will be further described with references to the drawings, wherein FIG. 10 is an exploded perspective view of components of a sensor assembly for pen device 100', FIG. 11 is a perspective view of the sensor assembly of FIG. 11 in the assembled state, FIG. 12 is a perspective view of a flexible carrier 160' of the sensor assembly shown in FIGS. 10 and 11.

In the figures like structures are mainly identified by like reference numerals.

DESCRIPTION OF EXEMPLARY EMBODIMENTS

When in the following relative expressions, such as "clockwise" and "counter-clockwise", "left" and "right", etc. are used, these refer to the appended figures and not necessarily to an actual situation of use. The shown figures are schematic representations for which reason the configuration of the different structures as well as their relative dimensions are intended to serve illustrative purposes only. When the term member or element is used for a given component it generally indicates that in the described embodiment the component is a unitary component, however, the same member or element may alternatively comprise a number of sub-components just as two or more of the described components could be provided as unitary components, e.g. manufactured as a single injection moulded part. The term "assembly" does not imply that the described components necessary can be assembled to provide a unitary or functional assembly during a given assembly procedure but is merely used to describe components grouped together as being functionally more closely related.

Figure 1:
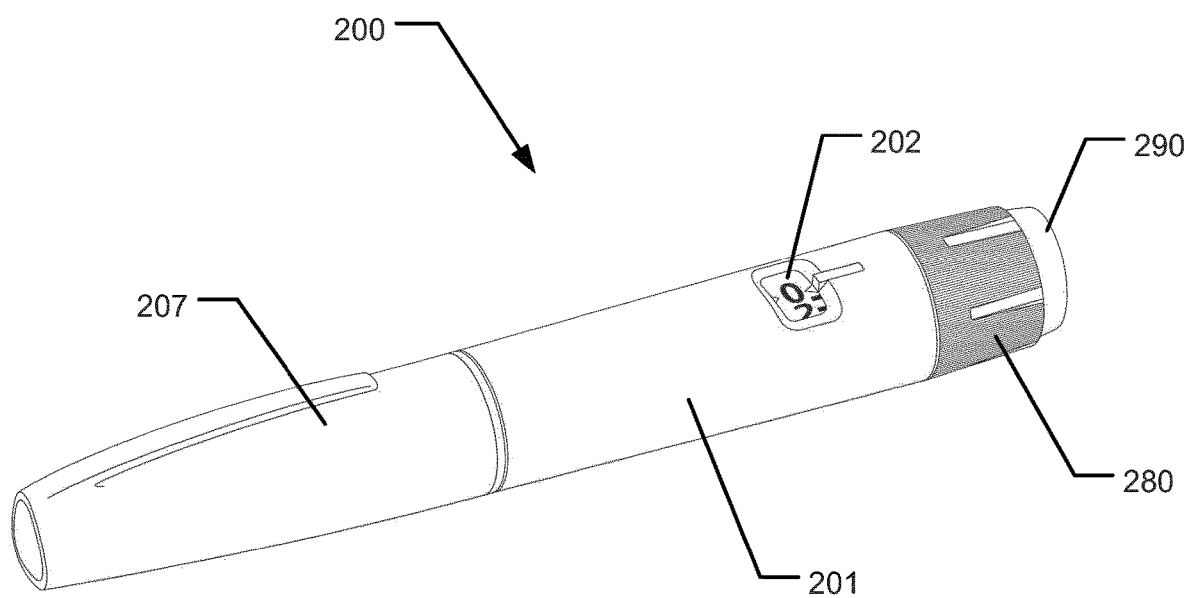
FIG. 1 shows a perspective view of a prior art pen device 200.
Figure 2:
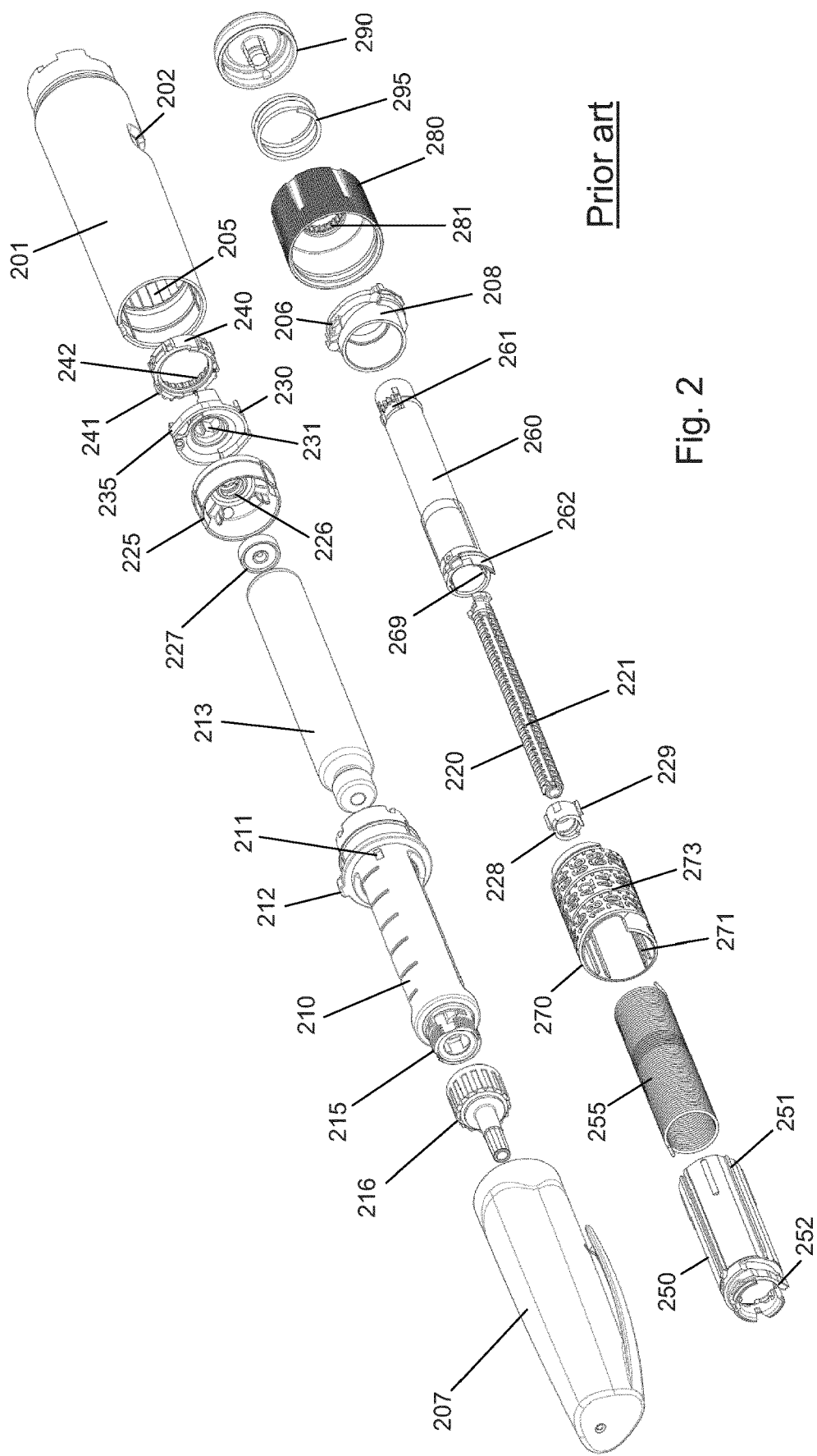
FIG. 2 shows in an exploded view the components of the pen device of FIG. 1, FIGS. 3A and 3B show in sectional views an expelling mechanism of the pen device of FIG. 1 in two states.
Figure 3A:
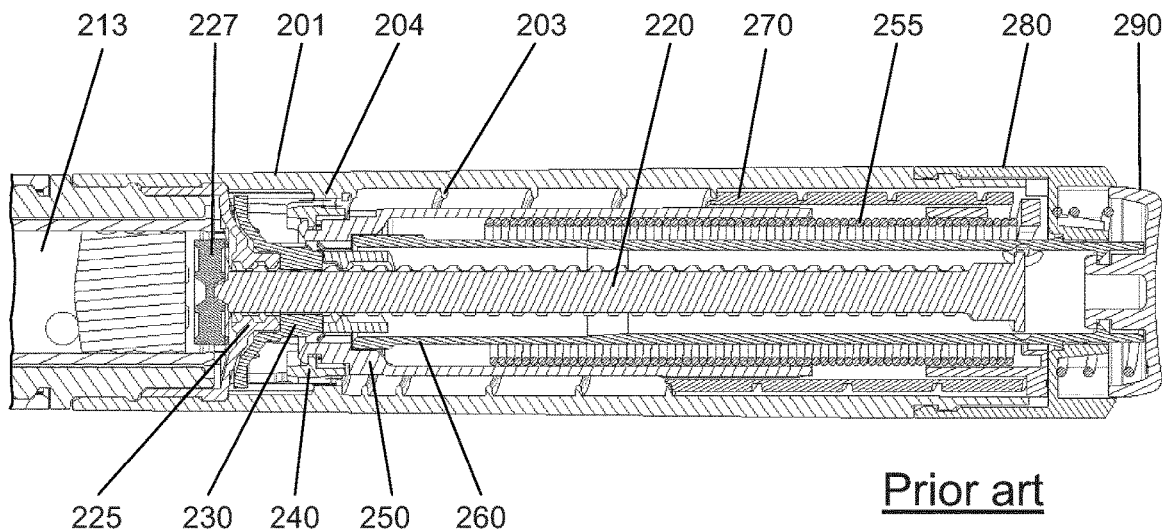
FIGS. 3C-3E show components of the pen device of FIG. 1.
Figure 3B:
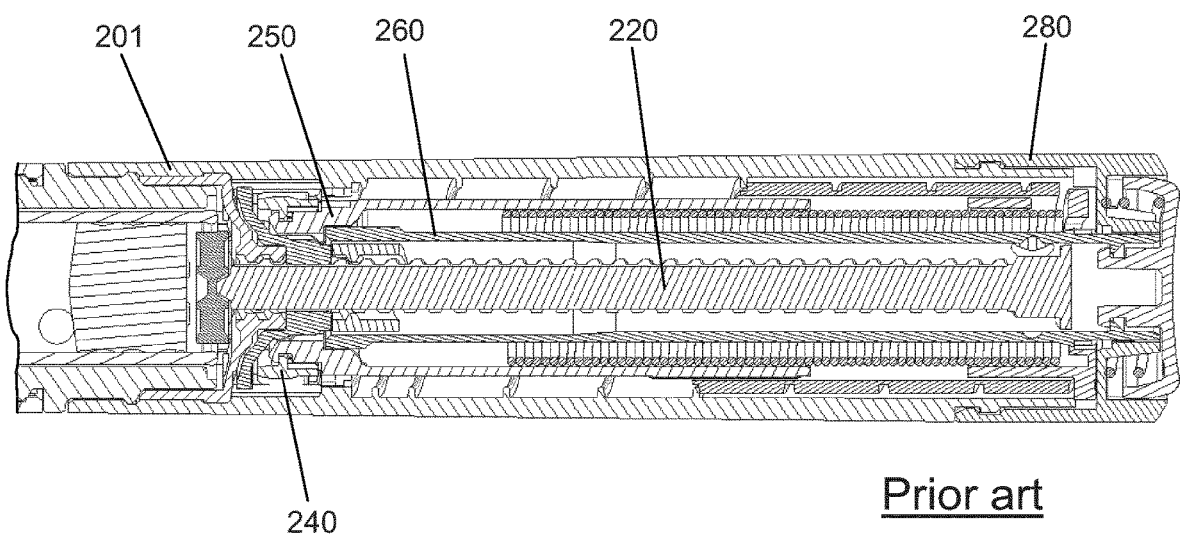

FIG. 1 shows a prior art drug delivery device in the form of a pen-formed auto-injection device 200, i.e. a so-called "injection pen" that includes an expelling mechanism incorporating a spring drive. FIG. 2 shows an exploded view of the prior art auto-injection device 200 shown in FIG. 1. FIGS. 3A and 3B show cross sectional views of the expelling mechanism of the prior art auto-injection device 200 shown in FIGS. 1 and 2 where FIG. 3A shows the device in dose setting state and FIG. 3B shows the device in dose expelling state.

In the present context the device 200 represents a "generic" drug delivery device providing a specific example of a device which, in accordance with the present invention, may be modified in order to obtain a device that provides electronic monitoring of movements within the drug delivery.

The pen device 200 comprises a cap part 207 and a main part having a proximal body or drive assembly portion with a housing 201 in which a drug expelling mechanism is arranged or integrated, and a distal cartridge holder portion in which a drug-filled transparent cartridge 213 with a distal needle-penetrable septum is arranged and retained in place by a nonremovable cartridge holder attached to the proximal portion, the cartridge holder having openings allowing a portion of the cartridge to be inspected as well as distal coupling means 215 allowing a needle assembly to be releasably mounted. The cartridge is provided with a piston driven by a piston rod forming part of the expelling mechanism and may for example contain an insulin, GLP-1 or growth hormone formulation. A proximal-most rotatable dose dial member 280 serves to manually set a desired dose of drug shown in display window 202 and which can then be expelled when the release button 290 is actuated. Depending on the type of expelling mechanism embodied in the drug delivery device, the expelling mechanism may comprise a spring as in the shown embodiment which is strained during dose setting and then released to drive the piston rod when the release button 290 is actuated.

As appears, FIG. 1 shows a drug delivery device of the pre-filled type, i.e. it is supplied with a pre-mounted cartridge and is to be discarded when the cartridge has been emptied. In alternative embodiments, and in accordance with the present invention, the drug delivery device may be designed to allow a loaded cartridge to be replaced, e.g. in the form of a "rearloaded" drug delivery device in which the cartridge holder is adapted to be removed from the device main portion, or alternatively in the form of a "front-loaded" device in which a cartridge is inserted through a distal opening in the cartridge holder which is non-removable attached to the main part of the device.

More specifically, referring to FIG. 2, the pen comprises a tubular housing 201 with a window opening 202 and onto which a cartridge holder 210 is fixedly mounted, a drug-filled cartridge 213 being arranged in the cartridge holder. The cartridge holder is provided with distal coupling means 215 allowing a needle assembly 216 to be releasably mounted, proximal coupling means in the form of two opposed protrusions 211 allowing a cap 207 to be releasably mounted covering the cartridge holder and a mounted needle assembly, as well as a protrusion 212 preventing the pen from rolling on e.g. a table top. In the housing distal end a nut element 225 is fixedly mounted, the nut element comprising a central threaded bore 226, and in the housing proximal end a spring base member 208 with a central opening is fixedly mounted. A drive system comprises a threaded piston rod 220 having two opposed longitudinal grooves and being received in the nut element threaded bore, a ring-formed piston rod drive element 230 rotationally arranged in the housing, and a ring-formed clutch element 240 which is in rotational engagement with the drive element (see below), the engagement allowing axial movement of the clutch element. The clutch element is provided with outer spline elements 241 adapted to engage corresponding splines on the housing inner surface, this allowing the clutch element to be moved between a rotationally locked proximal position, in which the splines are in engagement, and a rotationally free distal position in which the splines are out of engagement. As just mentioned, in both positions the clutch element 240 is rotationally locked to the drive element 230. The drive element comprises a central bore with two opposed protrusions 231 in engagement with the grooves on the piston rod whereby rotation of the drive element results in rotation and thereby distal axial movement of the piston rod due to the threaded engagement between the piston rod and the nut element. The drive element further comprises a pair of opposed circumferentially extending flexible ratchet arms 235 adapted to engage corresponding ratchet teeth 205 arranged on the housing inner surface. The drive element and the clutch element comprise cooperating coupling structures rotationally locking them together but allowing the clutch element to be moved axially, this allowing the clutch element to be moved axially to its distal position in which it is allowed to rotate, thereby transmitting rotational movement from the dial system (see below) to the drive system. The interaction between the clutch element, the drive element and the housing will be shown and described in greater detail with reference to FIGS. 3C and 3D.

On the piston rod an end-of-content (EOC) member 228 (EOC limiter) is threadedly mounted and on the distal end a washer 227 is rotationally mounted. The EOC member comprises a pair of opposed radial projections 229 for engagement with the reset tube (see below).

The dial system comprises a ratchet tube 250, a reset tube 260, a scale drum 270 with an outer helically arranged row of dose numerals, a user-operated dose dial member 280 for setting a dose of drug to be expelled, a release button 290 and a torque spring 255 (see FIGS. 3A and 3B). The reset tube is mounted axially locked inside the ratchet tube but is allowed to rotate a few degrees (see below). The reset tube comprises on its inner surface two opposed longitudinal grooves 269 adapted to engage the radial projections 229 of the EOC member, whereby the EOC can be rotated by the reset tube but is allowed to move axially. The clutch element is mounted axially locked on the outer distal end portion of the ratchet tube 250, this providing that the ratchet tube can be moved axially in and out of rotational engagement with the housing via the clutch element. The dose dial member 280 is mounted axially locked but rotationally free on the housing proximal end, the dose dial member being under normal operation rotationally locked to the reset tube (see below), whereby rotation of dose dial member results in a corresponding rotation of the reset tube and thereby the ratchet tube. The release button 290 is axially locked to the reset tube but is free to rotate. A return spring 295 provides a proximally directed force on the button and the thereto mounted reset tube. The scale drum 270 is arranged in the circumferential space between the ratchet tube and the housing, the drum being rotationally locked to the ratchet tube via cooperating longitudinal splines 251, 271 and being in rotational threaded engagement with the inner surface of the housing via cooperating thread structures 203, 273, whereby the row of numerals passes the window opening 202 in the housing when the drum is rotated relative to the housing by the ratchet tube. The torque spring is arranged in the circumferential space between the ratchet tube and the reset tube and is at its proximal end secured to the spring base member 208 and at its distal end to the ratchet tube, whereby the spring is strained when the ratchet tube is rotated relative to the housing by rotation of the dial member. A ratchet mechanism with a flexible ratchet arm 252 is provided between the ratchet tube and the clutch element, the latter being provided with an inner circumferential teeth structures 242, each tooth providing a ratchet stop such that the ratchet tube is held in the position to which it is rotated by a user via the reset tube when a dose is set. In order to allow a set dose to be reduced a ratchet release mechanism 262 is provided on the reset tube and acting on the ratchet tube, this allowing a set dose to be reduced by one or more ratchet increments by turning the dial member in the opposite direction, the release mechanism being actuated when the reset tube is rotated the above-described few degrees relative to the ratchet tube.

Having described the different components of the expelling mechanism and their functional relationship, operation of the mechanism will be described next with reference mainly to FIGS. 3A and 3B.

The pen mechanism can be considered as two interacting systems, a dose system and a dial system, this as described above. During dose setting the dial mechanism rotates and a torsion spring of the spring drive is loaded. The dose mechanism is locked to the housing and cannot move. When the push button is pushed down, the dose mechanism is released from the housing and due to the engagement to the dial system, the torsion spring will now rotate back the dial system to the starting point and rotate the dose system along with it.

The central part of the dose mechanism is the piston rod 220, the actual displacement of the piston being performed by the piston rod. During dose delivery, the piston rod is rotated by the drive element 230 and due to the threaded interaction with the nut element 225 which is fixed to the housing, the piston rod moves forward in the distal direction. Between the rubber piston and the piston rod, the piston washer 227 is placed which serves as an axial bearing for the rotating piston rod and evens out the pressure on the rubber piston. As the piston rod has a non-circular cross section where the piston rod drive element engages with the piston rod, the drive element is locked rotationally to the piston rod, but free to move along the piston rod axis. Consequently, rotation of the drive element results in a linear forwards movement of the piston. The drive element is provided with small ratchet arms 234 which prevent the drive element from rotating clockwise (seen from the push button end). Due to the engagement with the drive element, the piston rod can thus only move forwards. During dose delivery, the drive element rotates anti-clockwise and the ratchet arms 235 provide the user with small clicks due to the engagement with the ratchet teeth 205, e.g. one click per unit of insulin expelled.

Turning to the dial system, the dose is set and reset by turning the dose dial member 280. When turning the dial, the reset tube 260, the EOC member 228, the ratchet tube 250 and the scale drum 270 all turn with it. As the ratchet tube is connected to the distal end of the torque spring 255, the spring is loaded. During dose setting, the arm 252 of the ratchet performs a dial click for each unit dialed due to the interaction with the inner teeth structure 242 of the clutch element. In the shown embodiment the clutch element is provided with 24 ratchet stops providing 24 clicks (increments) for a full 360 degrees rotation relative to the housing. The spring is preloaded during assembly which enables the mechanism to deliver both small and large doses within an acceptable speed interval. As the scale drum is rotationally engaged with the ratchet tube, but movable in the axial direction and the scale drum is in threaded engagement with the housing, the scale drum will move in a helical pattern when the dial system is turned, the number corresponding to the set dose being shown in the housing window 202.

The ratchet 252, 242 between the ratchet tube and the clutch element 240 prevents the spring from turning back the parts. During resetting, the reset tube moves the ratchet arm 252, thereby releasing the ratchet click by click, one click corresponding to one unit IU of insulin in the described embodiment. More specifically, when the dial member is turned clockwise, the reset tube simply rotates the ratchet tube allowing the arm of the ratchet to freely interact with the teeth structures 242 in the clutch element. When the dial member is turned counter-clockwise, the reset tube interacts directly with the ratchet click arm forcing the click arm towards the centre of the pen away from the teeth in the clutch, thus allowing the click arm on the ratchet to move "one click" backwards due to torque caused by the loaded spring.

To deliver a set dose, the release button 290 is pushed in the distal direction by the user as shown in FIG. 3B. The reset tube 260 decouples from the dial member and subsequently the clutch element 240 disengages the housing splines 204. Now the dial mechanism returns to "zero"

together with the drive element 230, this leading to a dose of drug being expelled. It is possible to stop and start a dose at any time by releasing or pushing the push button at any time during drug delivery. A dose of less than 5 IU normally cannot be paused, since the rubber piston is compressed very quickly leading to a compression of the rubber piston and subsequently delivery of insulin when the piston returns to the original dimensions.

The EOC feature prevents the user from setting a larger dose than left in the cartridge. The EOC member 228 is rotationally locked to the reset tube, which makes the EOC member rotate during dose setting, resetting and dose delivery, during which it can be moved axially back and forth following the thread of the piston rod. When it reaches the proximal end of the piston rod a stop is provided, this preventing all the connected parts, including the dial member, from being rotated further in the dose setting direction, i.e. the now set dose corresponds to the remaining drug content in the cartridge.

The scale drum 270 is provided with a distal stop surface adapted to engage a corresponding stop surface on the housing inner surface, this providing a maximum dose stop for the scale drum preventing all the connected parts, including the dial member, from being rotated further in the dose setting direction. In the shown embodiment the maximum dose is set to 80 IU. Correspondingly, the scale drum is provided with a proximal stop surface adapted to engage a corresponding stop surface on the spring base member, this preventing all the connected parts, including the dial member, from being rotated further in the dose expelling direction, thereby providing a "zero" stop for the entire expelling mechanism. In the following, the position that the dial member assumes after completion of the expelling of a set dose will be referred to as the "zero dose position".

To prevent accidental over-dosage in case something should fail in the dialing mechanism allowing the scale drum to move beyond its zero-position, the EOC member serves to provide a security system. More specifically, in an initial state with a full cartridge the EOC member is positioned in a distal-most axial position in contact with the drive element. After a given dose has been expelled the EOC member will again be positioned in contact with the drive element. Correspondingly, the EOC member will lock against the drive element in case the mechanism tries to deliver a dose beyond the zero-position. Due to tolerances and flexibility of the different parts of the mechanism the EOC will travel a short distance allowing a small "over dose" of drug to be expelled, e.g. 3-5 IU of insulin.

The expelling mechanism further comprises an end-of-dose (EOD) click feature providing a distinct feedback at the end of an expelled dose informing the user that the full amount of drug has been expelled. More specifically, the EOD function is made by the interaction between the spring base and the scale drum. When the scale drum returns to zero, a small click arm 206 on the spring base is forced backwards by the progressing scale drum. Just before "zero" the arm is released and the arm hits a countersunk surface on the scale drum.

The shown mechanism is further provided with a torque limiter in order to protect the mechanism from overload applied by the user via the dose dial member. This feature is provided by the interface between the dose dial member and the reset tube which as described above are rotationally locked to each other. More specifically, the dose dial member is provided with a circumferential inner teeth structure 281 engaging a number of corresponding teeth arranged on a flexible carrier portion 261 of the reset tube. The reset tube teeth are designed to transmit a torque of a given specified maximum size, e.g. 150-300 Nmm, above which the flexible carrier portion and the teeth will bend inwards and make the dose dial member turn without rotating the rest of the dial mechanism. Thus, the mechanism inside the pen cannot be stressed at a higher load than the torque limiter transmits through the teeth.

Figure 3C:
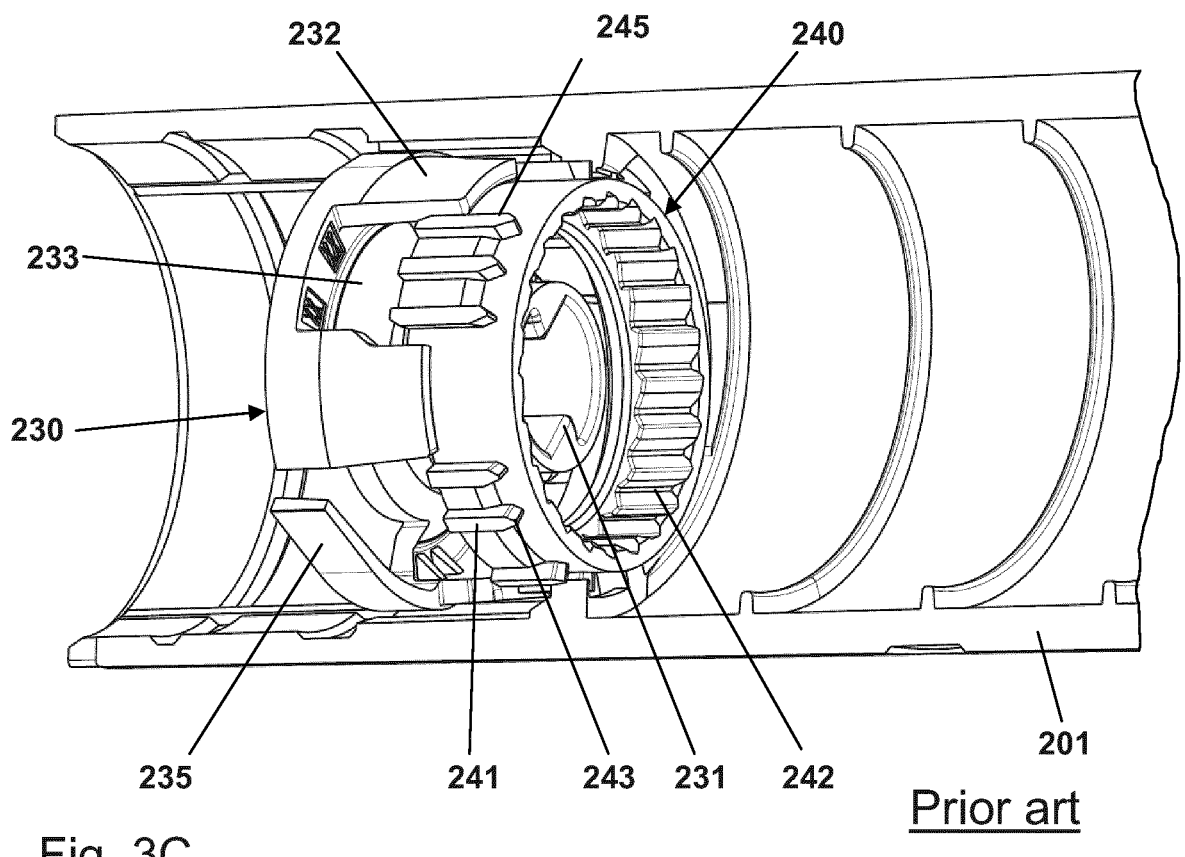
Figure 3D:
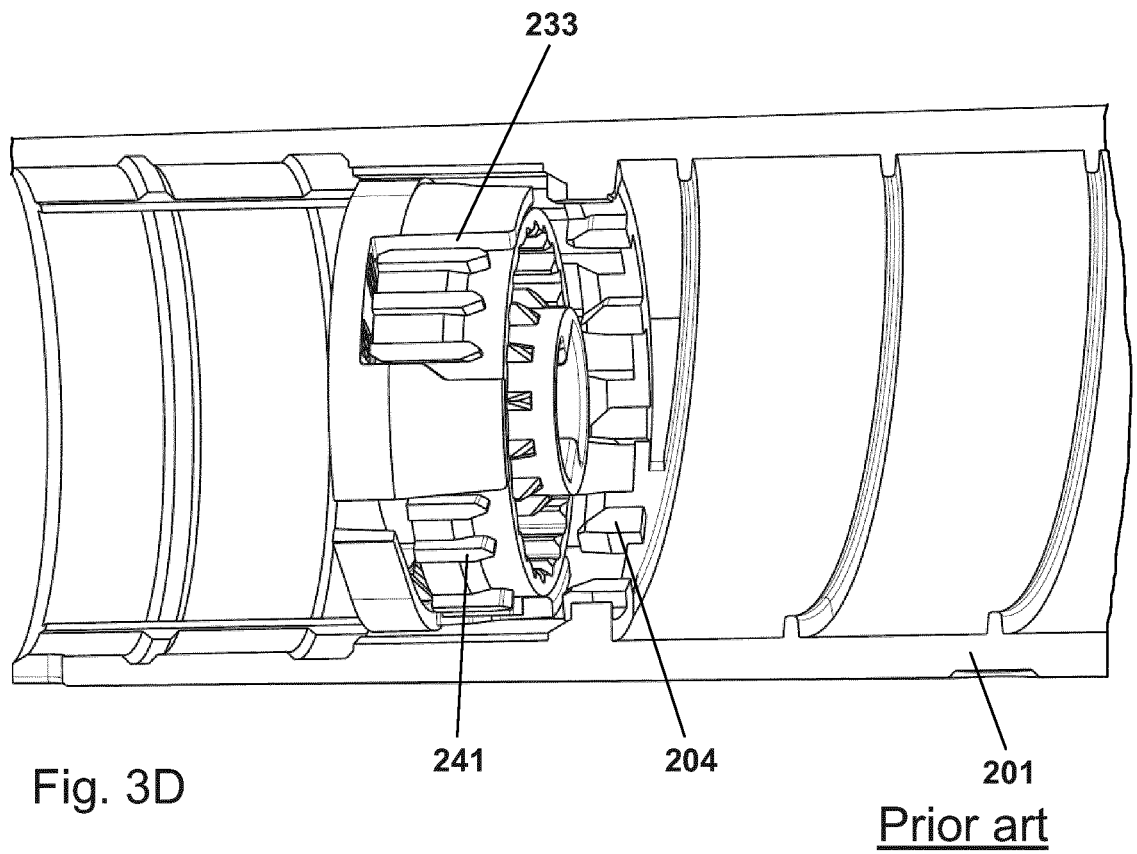
Figure 3E:
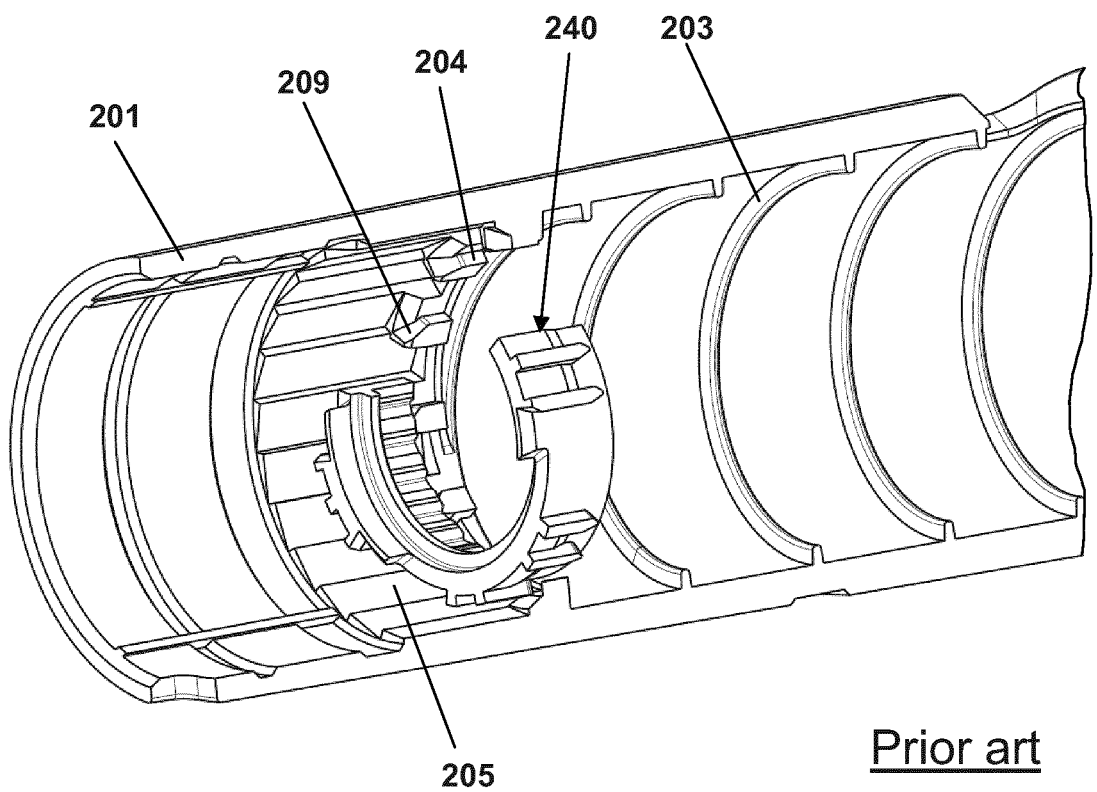

In FIG. 3C the clutch element, the drive element and the housing (in partial) are shown in the dose setting state, and in FIG. 3D the same components are shown in the expelling state. As appears, the piston rod on which the drive element is arranged and the ratchet tube on which the clutch element is mounted are not shown. To better show the structures provided on the inner surface of the housing FIG. 3E shows a partial clutch element 240 arranged in the housing 201.

The inner surface of the housing 201 comprises a circumferential ring-formed array of axially oriented spline elements 204 protruding into the interior, each having a pointed distal end 209, as well as a circumferential ring-formed array of one-way ratchet teeth 205. The inner surface further comprises a male helical thread 203 adapted to engage the female helical thread 273 on the scale drum 270. A distal circumferential groove is formed to engage and mount the nut element 225. The clutch element 240 comprises an inner circumferential ring-formed array of ratchet teeth 242 adapted to engage the ratchet arm 252 on the ratchet tube 250, and an outer circumferential ring-formed array of axially oriented spline elements 241 adapted to engage the spline elements 204 of the housing as well as the coupling slots in the drive element (see below), each spline having a pointed proximal end 243. The drive element 230 comprises a pair of opposed coupling portions each comprising two proximally extending skirt portions 232 between which an axially extending coupling slot 233 is formed, the slot being adapted to engage a portion of the clutch element spline elements. In this way the engaging surfaces serve to transmit a rotational force and thereby torque from the clutch element to the drive element in the expelling state. The drive element further comprises a pair of opposed circumferentially extending flexible ratchet arms adapted to engage the ring-formed array of one-way ratchet teeth 205. During dose delivery, the drive element rotates anti-clockwise and the ratchet arms 235 also provide the user with small clicks due to the engagement with the ratchet teeth 205, e.g. one click per unit of insulin expelled. In the shown embodiment 24 ratchet teeth are provided corresponding to 15 degrees rotation per unit of insulin. The central bore of the drive element comprises two opposed protrusions 231 adapted to engage with the axially oriented grooves on the piston rod.

In the dose setting state shown in FIG. 3C the spline elements 241 of the clutch element are in engagement with the spline elements 204 of the housing thereby rotationally locking the clutch element relative to the housing. As can be seen from FIG. 3C a group of clutch spline elements are received in the corresponding coupling slot with a slight rotational play. In the expelling state shown in FIG. 3D the spline elements 241 of the clutch element are moved distally out of engagement with the spline elements 204 of the housing thereby allowing rotation of the clutch element relative to the housing. As can be seen from FIG. 3D the group of clutch spline elements are now received in the corresponding coupling slot without rotational play.

FIG. 3C shows the clutch element 240 showing the above-described inner circumferential ring-formed array of ratchet teeth 242 and the outer circumferential ring-formed array of axially oriented spline elements 241. As appears, the spline elements are not arranged equidistantly on the ring but in groups, the groups comprising two opposed coupling groups 245 serving as the coupling means engaging the coupling slots 233. Whereas thus only some of the spline elements serve as coupling means between the clutch element and the drive element they all serve as coupling means between the clutch element and the housing splines 204.

Figure 4:
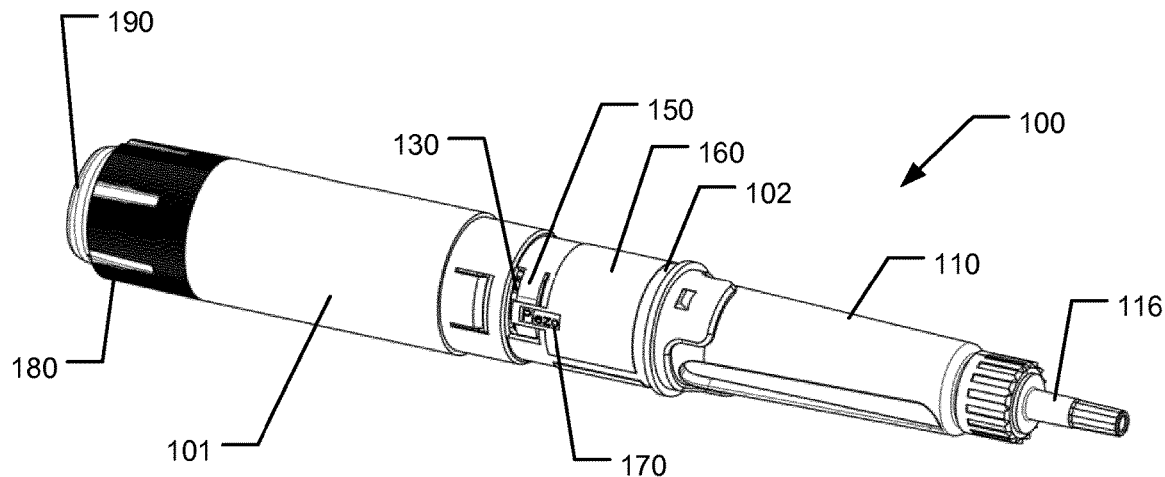
FIG. 4 is a perspective external view of an exemplary pen device 100 in accordance with a first embodiment of the invention, wherein a housing component has been omitted rendering deflectable transducer 170 visible.
Figure 5:
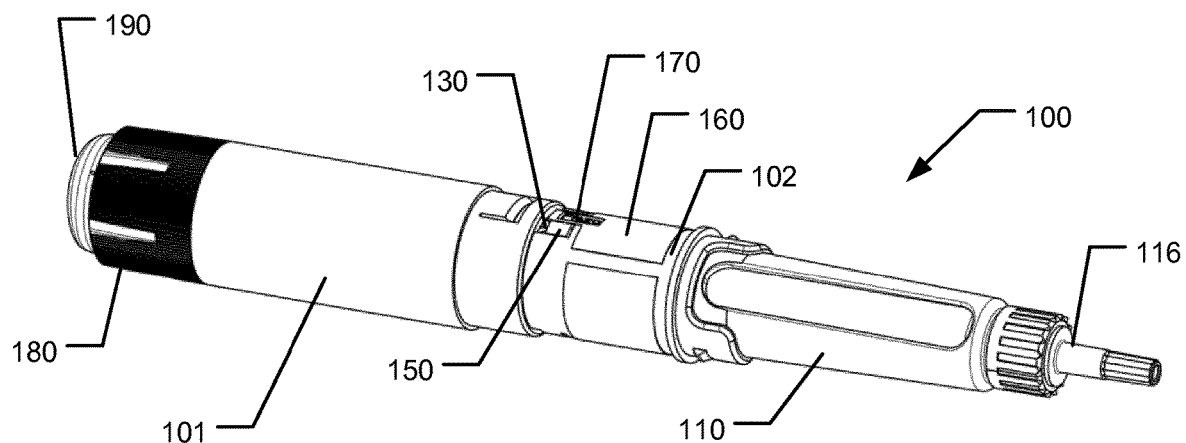
FIG. 5 is a similar view from a different angle, FIG. 6 schematically depicts a flexible substrate with electronic circuitry of the pen device 100, the substrate including a piezoelectric transducer.
Figure 6:
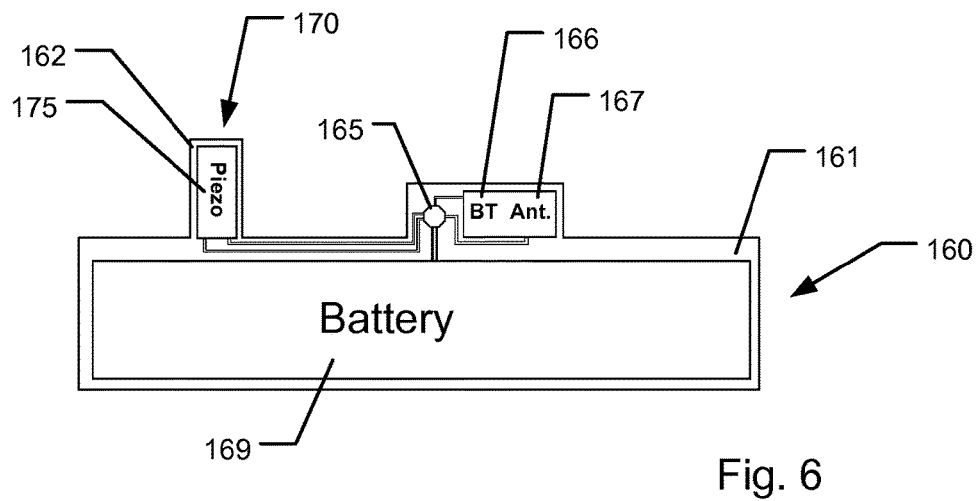
Figure 7:
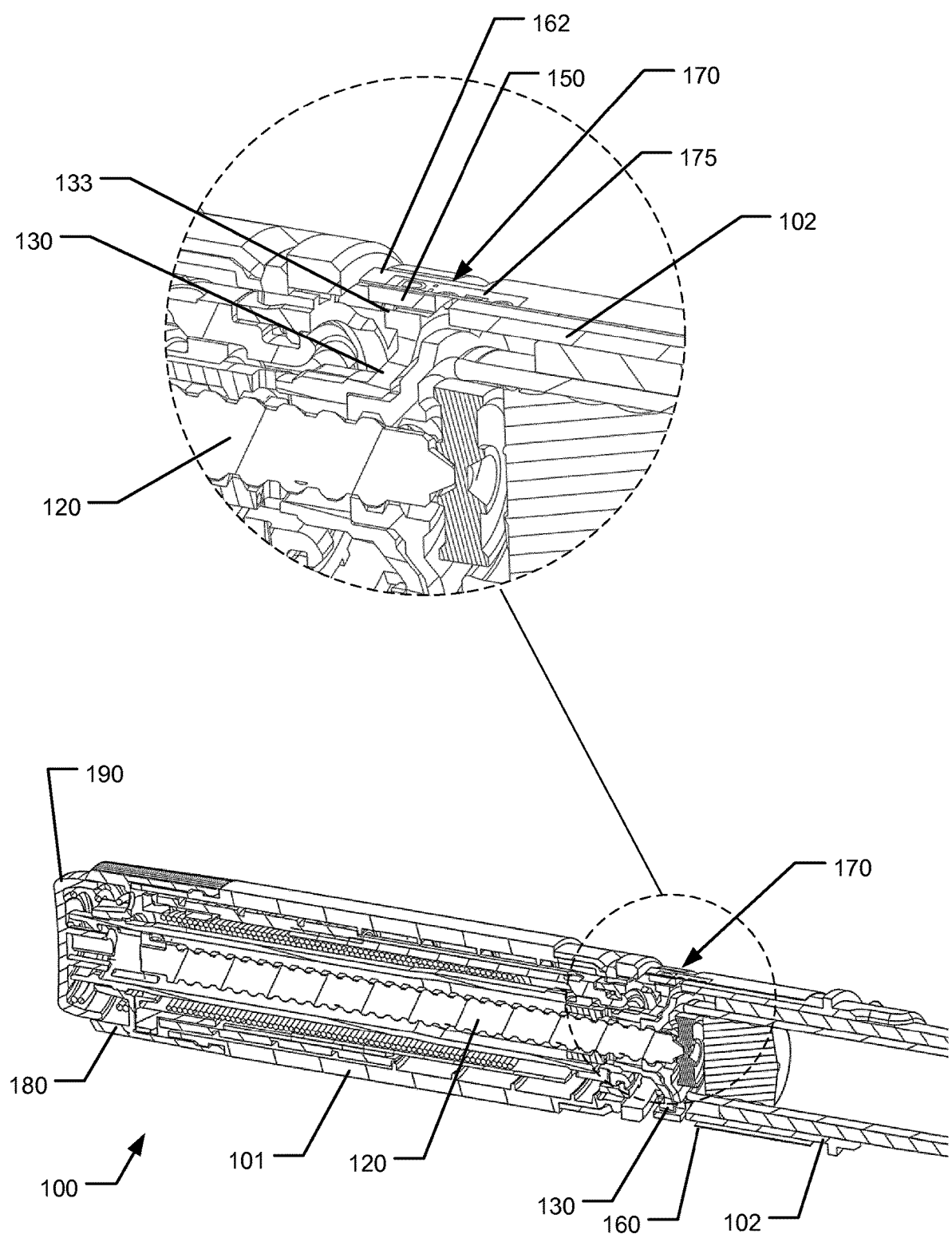
FIG. 7 is a perspective sectional view of the rear portion of a pen device 100 of the first embodiment.

FIGS. 4 through 7 show a pen injection device 100 according to a first exemplary embodiment of the present invention. FIGS. 4 and 5 provide first and second perspective external views of device 100 from different angles. Similarly to the prior art pen injection device 200 described above, the pen injection device 100 comprises a tubular housing 101, a proximal-most rotatable dose dial member 180, a push-button 190, and an injection needle 116 attached at the distal end of the device. Relative to the prior art injection device 200 injection device 100 includes a modified housing structure which includes reduced length tubular housing 101 arranged at the proximal end and an additional intermediate housing section 102 arranged distally of housing 101. The housing section 102 encircles a portion of the expelling assembly and provides a radially outwards facing cylindrical surface. For illustrative purposes, FIGS. 4, 5 and 7 depict the device 100 with an additional part of the housing omitted so as to reveal details of the housing section 102. In the final version of the pen injection device 100, the not shown additional part of the housing, i.e. a sleeve formed component, is intended to be mounted over the reduced diameter portion of housing section 102 so that, for the fully assembled device, the proximal portion of the device assumes a near-cylindrical appearance.

The radially outwards facing cylindrical surface of housing section 102 includes parallel circumferentially running slit-shaped through going openings which enable a material portion connected to the remainder of housing section 102 to define a resilient deflectable arm 150. Resilient deflectable arm 150 thus partly encircles the expelling assembly and has a free end which is resiliently deflectable in the radially outwards direction. Close inspection of FIGS. 4 and 5, at the area of deflectable arm 150, reveals that a rotatable element 130 is arranged at an axial position enabling a radial outwards facing surface to cooperate with deflectable arm 150. Rotatable element 130 is mounted axially fixed relative to housing but may be forced to rotate by the spring drive of the device.

Functionally, rotatable element 130 largely corresponds to the drive element 230 of the prior art pen injection device 200 described above. Hence, rotatable element 130 rotates during expelling in a manner wherein the amount of rotation is proportional to the size of the dose that is expelled from the device.

Referring to FIG. 7 which shows a perspective sectional view of the proximal portion of pen device 100, the rotatable element 130 defines a toothed wheel arranged rotatable around the longitudinal axis of the pen device, the rotatable element 130 having a protrusion configuration comprising a plurality of serially disposed protrusions 133 protruding radially outwards. The protrusions 133 are equally spaced along the circumference of rotatable element 130. In FIG. 7, the rotatable element is configured for being driven in anti-clockwise direction only (seen from the push-button end of the device). Each protrusion 133 is formed with a gradually rising leading side and a sharply dropping trailing side. In the shown embodiment the protrusion configuration of the rotatable element 130 defines protrusions being spaced with angular steps of 15 deg., meaning that twenty-four protrusions are distributed evenly around the circumference. Between any two neighbouring protrusions 133 the first element defines a bottom level in the valleys, whereas the peaks of the protrusions 133 define a top level.

Resilient deflectable arm 150 includes at its deflectable end a radially inwards pointing geometry configured for riding over the protrusions 133 of rotatable element 130 as the rotatable element is turned during expelling. Resilient deflectable arm 150 are radially movable from a relatively unbiased radial first position when the engaging geometry of the arm is located between neighbouring protrusions 133, i.e. at the bottom level, and into a biased radial second position when the engaging geometry of the arm is located upon a top portion of a protrusion 133. The housing section 102 will typically be formed from a polymeric material with the resilient deflectable arm being unitarily moulded with the remaining portion of the housing section 102. In the shown embodiment, the resilient deflectable arm 150 remains in intimate contact with the outer contour of the rotatable element 130 including the valleys between protrusions. The resilient deflectable arm 150 is thus configured to resiliently deflect in the protruding direction, i.e. radially outwards, upon cooperation with the protrusions of the rotatable element with the number of oscillations proportional with the size of the expelled dose.

In the shown embodiment, in accordance with the invention and also referring to FIG. 6, to enable monitoring operation of the device by electronic means, an electronic circuitry 160 is arranged partly on and partly inside the device 100 for registering events associated with operations performed by the device. The electronic circuitry will typically include a processor 165, an energy source such as a battery, and at least one sensor 170 for monitoring movements of one or more components within the drug injection device. In the shown embodiment, the electronic circuitry 160 also includes a printed battery 169, communication means, e.g. antenna 167 and communication circuitry 166, such as Bluetooth unit, for communicating registered events to an external device, such as a Smartphone. Although not incorporated in the shown embodiment, the electronic circuitry may in other embodiments further include a display so as to offer a visible read-out of information related to registered events.

In the shown embodiment, the electronic circuitry 160 is provided as a flexible sheet 161 formed as a flexible electronic label, that includes printed circuitry including piezoelectric sensor material 175 printed onto the flexible sheet. In the shown embodiment, the flexible sheet 161 is provided as a carrier foil formed by a polymeric material, such as PET, with a thickness of approximately 125 microns, e.g. a PET foil selected as a material exhibiting a modulus of elasticity in the order of 1.000-20.000 MPa. Such material is particularly suitable for a piezoelectric sensor arrangement in accordance with the invention. In other embodiments, the electronic circuitry may be configured in other ways, e.g. with some of the electronic components being disposed in other ways than by printing onto flexible sheet 161. For example, discrete electronic components may be arranged outside the housing or fully or partly within housing 101/102 with the discrete components being electronically connected to sensor 170 on the flexible sheet 161.

In the shown embodiment, the sensor 170 is provided as an active deflectable transducer incorporating a tab 162 extending from the flexible sheet 161 towards a free tab end and having piezo-electric material 175 disposed onto the tab 162. Referring to FIG. 7, the electronic circuitry 160 is formed as a flexible sheet 161 provided as an adhesive label that wraps around and adheres to the outer surface of housing section 102. The flexible sheet 161 is mounted so that the tab 162 angularly aligns with the free end of resilient deflectable arm 150 but arranged at a right angle relative to the longitudinal direction of the resilient deflectable arm 150. In the shown embodiment, the tab 162 thus spans across the above described parallel circumferentially running slit-shaped through going openings arranged on either side of the resilient deflectable arm 150. In other embodiments, the tab 162 only spans from areas of the flexible sheet carrying 161 electronic circuit portion across a single circumferentially running slit-shaped opening towards the free end of the tab, whereby the free end of the tab 162 is supported, at least momentarily during expelling, by the resilient deflectable arm 150.

The tab 162 is not adhered to the resilient deflectable arm 150 but is allowed to become deflected slightly away from upper surface of the resilient deflectable arm 150. However, in the shown embodiment, all other portions of the flexible sheet 161 are attached to the housing section 102, and the base of the tab 162 thus defines a base portion of the deflectable transducer 170 that is arranged non-movably in the protruding direction, i.e. the radial direction. The tip end of the free tab 162 provides a deflectable portion of the carrier foil that deflects relative to the base portion in the protruding direction upon engaging cooperation with protrusions of the rotatable element 130.

In the shown embodiment, the resilient deflectable arm 150 acts as an activation arm arranged between the rotatable element 130 and the deflectable transducer 170, wherein the deflectable end of the carrier foil cooperates with the deflectable end of the activation arm by direct engagement. Hence, the deflectable portion of the deflectable transducer 170 deflects radially outwards relative to the base portion upon cooperation between the resilient deflectable arm 150 with protrusions 133 of the rotatable element 130. In accordance with the deflection, the piezo-electric sensor material 175 generates an activation signal for each protrusion 133 that passes the deflectable arm 150.

The piezo-electric sensor material 175 is disposed onto the tab 162 so that it extends from the tip end of tab 162 to a portion of the base portion of the carrier foil (see FIG. 7, enlarged portion). Hence, the carrier foil, between the base portion and tip end of the deflectable portion, includes a non-supported portion having piezo-electric sensor material 175 disposed at least partly along the non-supported portion. By forming the carrier foil with foil portions to be non-supported by other components, i.e. except for the strain sensitive material itself, the strain sensitive material disposed along the non-supported portion of the carrier foil is therefore exclusively supported by the carrier foil. This is in contrast with prior art systems where a piezo-electric element is attached to a support structure, such as a flexible beam, and thus being supported by additional structures having additional weight, differing bending properties, as well as various other mechanical properties influencing the dynamic properties of the deflectable transducer.

With reference to FIGS. 8-11, details with respect to a pen device 100' in accordance with a second embodiment of the invention will now be described. The pen device 100' corresponds to the pen device 100 of the first embodiment in most aspects, however with features differing from pen device 100 as described in the following.

Figure 8:
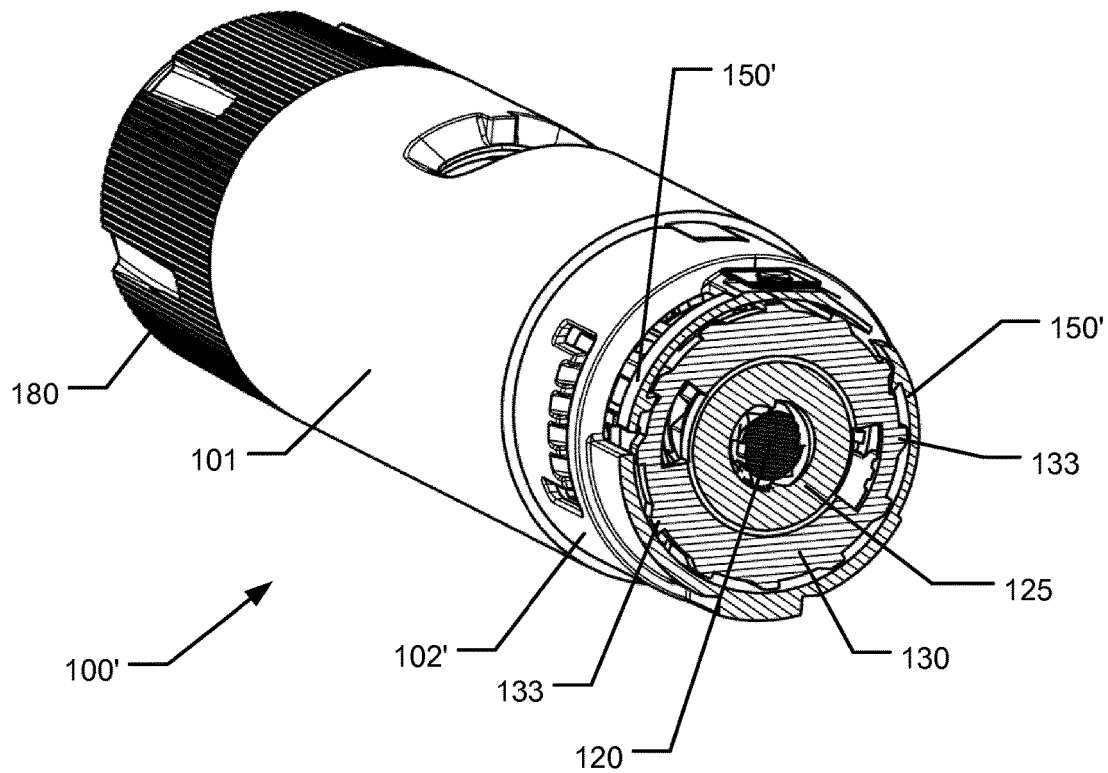
FIG. 8 is a cross sectional view of a second embodiment of a pen device 100' in accordance with of the invention.

Again, as shown in FIG. 8, a rotatable element 130 defines a toothed wheel arranged rotatable around the longitudinal axis of the pen device, the rotatable element 130 having serially disposed protrusions 133 protruding radially outwards. In the second embodiment two resilient deflectable arms 150 are arranged at different circumferential locations around the axis of the pen device, each arm including at its deflectable end a radially inwards pointing geometry configured for riding over the protrusions 133 of rotatable element 130 as the rotatable element is turned during expelling.

Instead of having an electronic circuitry provided as a flexible electronic label that adheres relative to the housing structure of the pen device, the second embodiment includes an electronic circuitry 160' provided as a flexible carrier 161 that is retained with respect to the housing structure by means of a clamping element. The flexible carrier 161 is shown most clearly in FIG. 12.

As disclosed in co-pending patent application WO2018EP83550 two or more sensors may be used for error mitigation, or simply to increase accuracy and reliability of detection of the drug expelling movement. In accordance herewith, the second embodiment of pen injection device 100' includes two independent sensors 170', each sensor provided as an active deflectable transducer arranged for cooperation with a respective one of the two deflectable arms 150'.

In the second embodiment, in order to provide an effective assembly process, the electronic circuitry is part of a sensor assembly which is depicted in FIG. 11. Once assembled, the sensor assembly may be tested, even in a state when not arranged relative to other pen device components. Furthermore, the sensor assembly may be easily handled during assembling operations. The components of the sensor assembly are shown in an exploded view depicted in FIG. 10, which shows a housing element 102', a battery 169' in the form of a coin cell, the electronic circuitry 160', and a retaining element 145'.

The housing element 102' is configured to couple to a modified proximal housing element 101, and is provided with the two deflectable arms 150'. Also in the shown second embodiment, the resilient deflectable arm 150 acts as an activation arm arranged between the rotatable element 130 and the deflectable transducer 170, wherein the deflectable end of a tab protruding from the flexible carrier 1611 cooperates with the deflectable end of the activation arm by direct engagement.

The housing element 102' is generally shaped as a sleeve and further includes a reduced diameter portion formed to provide a battery compartment for accommodating the battery 169', the reduced diameter portion further formed for accommodating the electronic circuitry 160' and the retaining element 145' in the order specified. The housing element 102' further comprises, at radially outwards facing surfaces, positioning geometries that includes a fixation pin 102'C and two pairs of clamping ribs 102'B arranged on diametrically opposed sides of the sleeve formed housing element 102'.

As shown in FIG. 12, the electronic circuitry 160' is again provided as a flexible sheet 161 onto which electronic components and conductive wirings are disposed, for example by means of a printing process. A positioning tab extends in the proximal direction, the positioning tab being provided with a hole 160'C arranged to cooperate with the fixation pin 102'C. Two tabs 162 extend proximally from the sheet, each of the tabs 162 being provided with piezo-electric material 175 disposed onto the tab so as to form a deflectable transducer 170' in a manner similar to the first embodiment. The flexible sheet 161 further comprises tab formed areas 160'D configured for being folded to electrically connect to the battery 169'.

Figure 9:
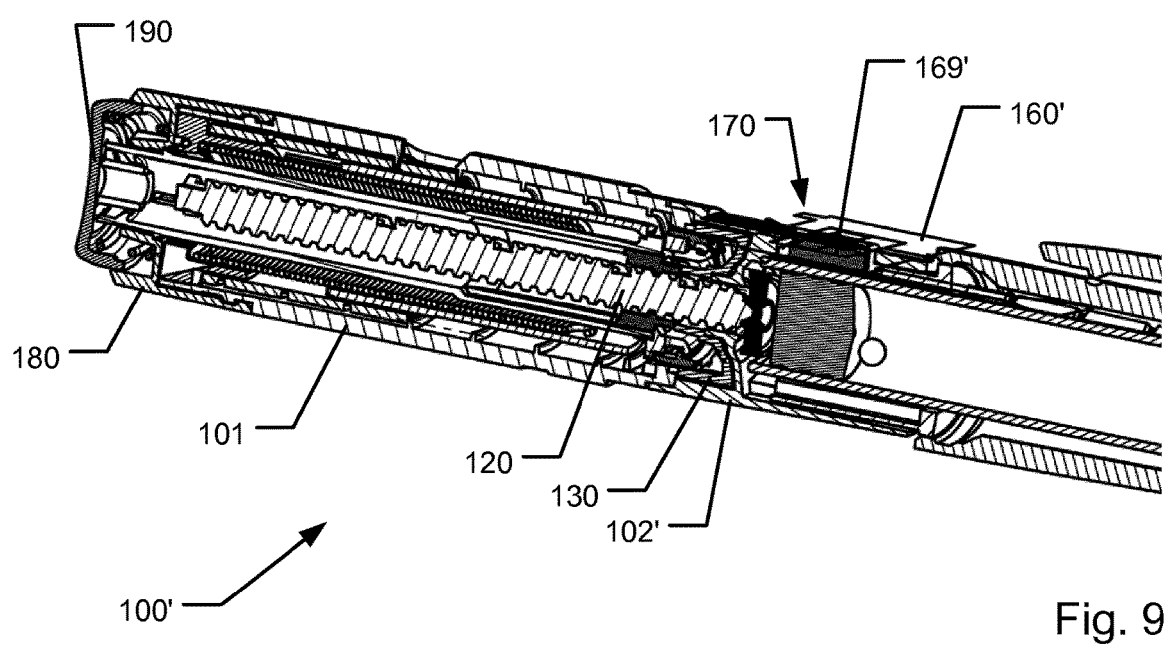
FIG. 9 is a perspective sectional view of key components of the rear portion of a pen device 100' during assembly.

In FIG. 9, which is a perspective sectional view of key components of the most proximal part of the injection pen 100', the electronic circuitry 160' is shown in an intermediate state where it assumes a planar configuration. The electronic circuitry 160' is depicted mating with the battery 169', and with one of the deflectable transducers 170' pointing in the proximal direction. However, referring to FIG. 10, the flexible sheet 161 of electronic circuitry 160' will be folded during assembly to assume a curved configuration so as to partly encircle housing element 102' and battery 169', while aligning the two tabs 162 with the two deflectable arms 150' of housing element 102' so that each tab 162 is positioned in contact with a radially outside surface of the respective deflectable arm 150'. The tab formed areas 160'D folds down next to side portions of the battery 169' to provide electrical contact between the flexible sheet 161 and both electrodes of the battery.

In accordance with an aspect of the present invention, in order to avoid using adhesives during production, and to provide superior long-term stability of the sensor assembly, the electronic circuitry 160' is retained onto housing element 102' by means of a retaining member in the form of a spring arrangement 145'. Spring arrangement 145' is formed from a single piece of stamped sheet made from spring steel which has been subsequently folded to assume the profile shown in FIG. 10. The spring arrangement 145' is depicted in the relaxed state. Spring arrangement 145' includes a positioning tab that extends in the proximal direction, the positioning tab being provided with a hole 145'C arranged to cooperate with the fixation pin 102'C. Further two positioning tabs 145'B extend circumferentially, each being configured to engage and lock relative to a respective one of the clamping ribs 102'B arranged on diametrically opposed sides of the sleeve formed housing element 102'. Further folded tabs 145'D of the spring arrangement 145' are configured to engage and retain the tab formed areas 160'D of the electronic circuitry 160' to provide contact between the flexible sheet 161 and the battery. Finally, two sensor retaining tabs 145'A are provided, each tab being formed to engage areas adjacent the respective tabs 162 of the flexible sheet 161 so as to provide intimate contact between each deflectable transducer 170' and it's respective designated deflectable arm 150'. Each of the tabs 145'A are formed to provide a biasing clamping force onto areas of the flexible sheet 161 so as urge the flexible sheet against areas of the housing element 102' which form a base of the respective deflectable arm 150'. Also tabs 145'D are formed to provide a biasing clamping force onto areas of the flexible sheet 161 so as urge the flexible sheet against the battery 169'.

Each sensor retaining tab 145'A is so configured that the tab only retains the base portion of the deflectable transducer 170' relative to a base portion of the deflectable arm 150'. Hence the free end of the deflectable transducer 170', i.e. the tab 162, is not engaged by the spring arrangement 145', and the free end of the deflectable transducer 170' is only held in engagement with its respective deflectable activation arm 150' due to the inherent rigidity of the flexible sheet 161.

In FIG. 11, the sensor assembly is shown in an assembled state, ready to be mated with an expelling assembly of the pen injection device 100'. One of the two deflectable transducers 170' is visible and is shown extending proximally relative to the spring arrangement 145' so that the free end of the transducer 170' engages the deflectable arm 150' without being engaged by the spring arrangement 145'. In the final configuration of the pen injection device 100' a not shown sleeve is configured to encircle the sensor assembly so as to protect the sensor assembly and to provide a smooth outer surface. The not shown sleeve is configured to engage non-referenced spring tabs extending radially outwards from the spring arrangement 145' in order to assist in holding spring arrangement 145' fixedly positioned onto housing element 102'.

Figure 13:
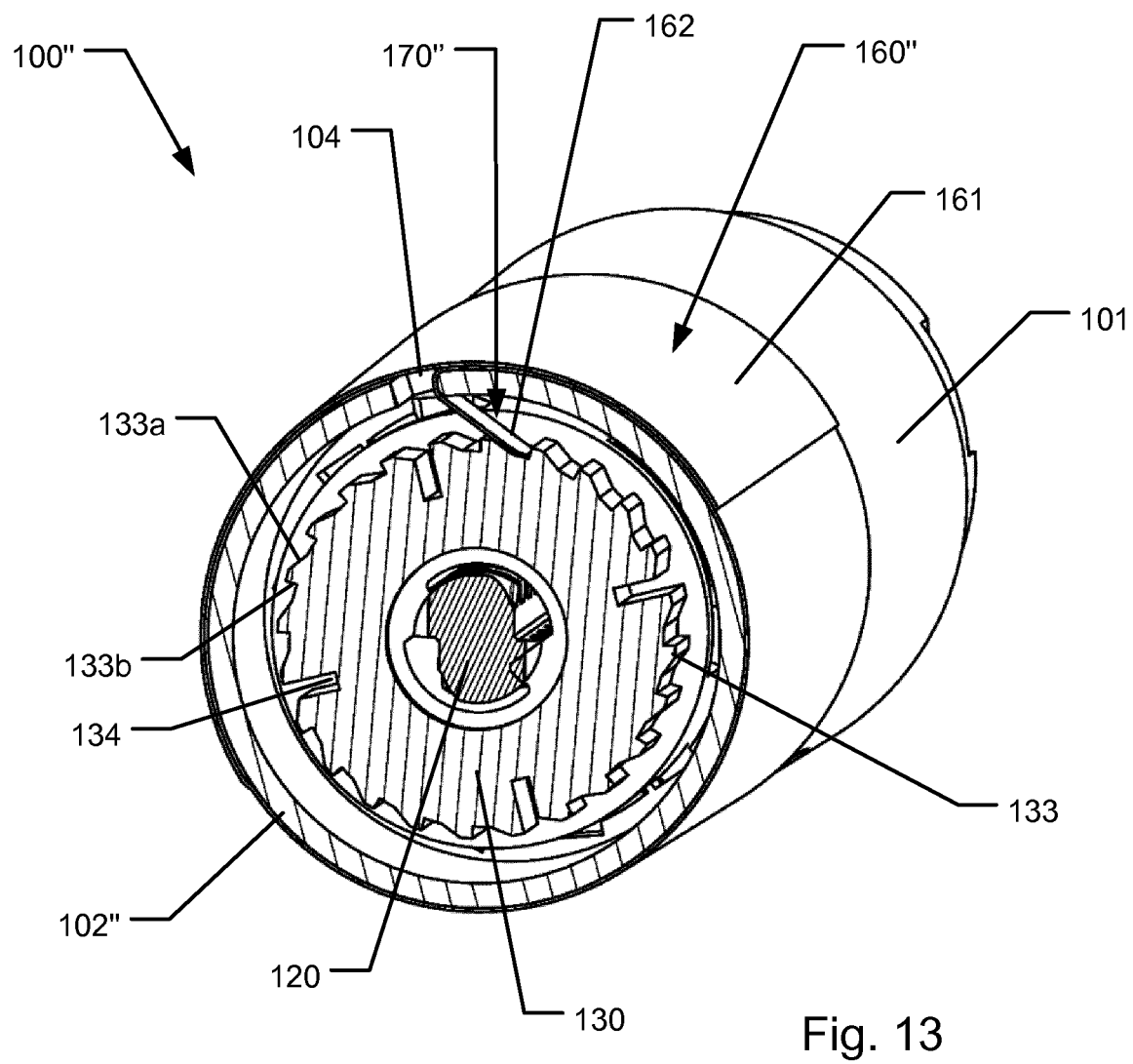
FIG. 13 is a cross sectional view of a third embodiment of a pen device 100" in accordance with the invention.

Reference is now made to FIG. 13 which shows a cross sectional view of a pen injection device 100" in accordance with a third embodiment of the invention. Again, similarly to the prior art pen injection device 200 described above, the pen injection device 100" comprises a tubular housing 101, a proximal-most rotatable dose dial member 180, a push-button arranged to protrude proximally. The device 100" may incorporate a similar drive mechanism as that incorporated in prior art device 200. FIG. 13 shows a cylindrical piston rod drive element 130 which rotates together with the piston rod 120 during expelling so that the rotatable element 130 experiences unidirectional rotational movement relative to the housing 101.

The rotatable element 130 defines a toothed wheel having a protrusion configuration comprising a plurality of serially disposed protrusions 133 protruding radially outwards. The protrusions are equally spaced along the circumference of rotatable element 130. In this embodiment, the rotatable element 130 is configured for being driven unidirectionally in anti-clockwise direction only (seen from the push-button end of the device). Each protrusion 133 is formed with a gradually rising leading side 133a and a sharply dropping trailing side 133b. In the shown embodiment the protrusion configuration of the rotatable element 130 defines protrusions being spaced with angular steps of 15 deg., meaning that twenty-four protrusions are distributed evenly around the circumference. Between any two neighbouring protrusions 133, rotatable element 130 defines a bottom level in the valleys, whereas the peaks of the protrusions 133 define a top level.

Also in this third embodiment, the electronic circuitry 160" is provided as a flexible sheet 161 forming a flexible adhesive electronic label that includes printed electronic circuitry comprising piezoelectric sensor material 175 printed onto the flexible sheet. In the shown embodiment, the flexible sheet 161 is provided as a carrier foil formed by a foil material, such as PET, with a thickness of approximately 125 microns, e.g. a PET foil selected as a material exhibiting a modulus of elasticity in the order of 1.000-20.000 MPa.

In the embodiment shown in FIG. 13, the sensor is provided as an active deflectable transducer 170" incorporating a free tab of the flexible sheet and having piezoelectric material disposed onto the tab. Referring to FIG. 13, the flexible sheet has been mounted so that it wraps around and adheres to the outer surface of housing 101. The flexible sheet has been mounted so that the free tab, and thus the main portion of the deflectable transducer 170", enters an axial slit-formed opening 104 formed in the housing 101 and protrudes inwardly towards the rotatable element 130, in a position where the deflectable transducer 170" is aligned axially with the rotatable element 130. The deflectable transducer 170" is of such length that the deflectable transducer is arrangeable, as shown in the operating state depicted in FIG. 13, so that it comprises a first segment extending counter to the rotational direction from a base portion outside the housing 101 to a bending portion and further comprises a second segment extending in a direction generally in the rotational direction from the bending portion to the tip end of the deflectable transducer 170". However, as the deflectable transducer 170" is configured to cooperate with the circumferential portion of the rotatable element 130 so that the tip portion of the deflectable transducer 170" assumes intimate contact with the gradually rising leading side 133a of a rotationally aligned protrusion 133, the second segment includes sub-segments that form angles within a range of 40 to 60 degrees relative to the first segment.

As in the first embodiment, the deflectable transducer comprises a non-supported portion for the carrier foil having said strain sensitive material disposed arranged along the unsupported portion, in this third embodiment the second segment. In the shown embodiment on FIG. 13, the piezo electric material is disposed at portions including the bending portion of the carrier foil on the radially inwards facing surface thereof, i.e. the concave portion between the first segment and the second segment.

To facilitate easy assembly, the shown embodiment includes a number of radial cut-outs forming axial passages 134 in the rotatable element 130. In the shown embodiment, four such axial passages are formed but other numbers of axial passages may be applicable as well. At least one such axial passage should be formed to benefit for the easy assembly method. The axial passages 134 allow the flexible sheet to be mounted prior to insertion of rotatable element 130. The passages 134 are of sufficient radial depth to allow the deflectable transducer 170" to remain in a passive resting state wherein the deflectable transducer extends radially inwards pointing towards the axis. When the rotatable element 130 is inserted into the assembly, the rotatable element 130 is initially angularly aligned with the deflectable transducer 170", and the rotatable element is easily inserted axially relative to the deflectable transducer so that the deflectable transducer is fully accommodated within the passage 134 in question. After assembly, the rotatable element 130 is rotated so that the deflectable transducer is brought out of the passage 134. Rotation is continued until the deflectable transducer 170" assumes the state shown in FIG. 13, whereafter the deflectable transducer 170" can be moved unidirectionally over all the protrusions 133 without dropping into any of the passages 134.

In certain embodiments, such as the above described devices 100, 100' and 100" according to the first, second and third embodiment, the processor 165 comprises a counter adapted to count the number of generated signals reflecting the number of dose units expelled from the device. The counter may in one embodiment use information from the single piezoelectric transducer to count expelled units. Alternatively, in other embodiments, the counter may additionally use information from additional piezoelectric transducers to count expelled units.

In the shown embodiment, the processor is configured to modify a value of the counter upon each protrusion passing the deflectable transducer 170, 170', 170".

The processor typically includes circuitry to keep track of time. In this way a log may be stored in a memory of the electronic circuitry so that the quantity of an expelled dose is stored together with a time parameter, such as a real-time value, or a relative time-stamp. A plurality of individual sets of stored quantities of expelled drug and associated time values may be stored for later retrieval. In the shown embodiment, the contents of the storage, i.e. the log, may be transferred to an external device, such as be wireless communication.

In other embodiments, the principle of using a deflectable transducer with a deflectable portion that comprises a non-supported portion having a strain sensitive material disposed at least partly along the non-supported portion may be utilized for monitoring movement of components within an injection device other than the described component moving during expelling. For example, instead or in addition to the described monitoring of a component that moves during expelling, a component that moves during dose setting may be monitored using the same principle.

Also, instead of monitoring movement of a rotatable component, or components that moves rotationally relative to each other, the described principle of monitoring movement may be used to monitor a linearly moved component in the device.

In the above description of exemplary embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. A drug injection device comprising:
   a first element and a second element configured to undergo relative movement in respect of each other, said movement corresponding to an action performed on or by the drug injection device and representing an amount of drug delivered or to be delivered from the drug injection device,
   wherein the first element comprises a plurality of protrusions serially disposed along a trajectory of said relative movement, the protrusions protruding in a protruding direction,
   wherein the second element comprises a second element base, and at least one deflectable transducer configured for sequentially cooperating with the plurality of protrusions of the first element to generate an activation signal as the at least one deflectable transducer is deflected in the protruding direction when travelling past each protrusion, wherein the at least one deflectable transducer defines a base portion attached to the second element base, the base portion being non-movably arranged in the protruding direction relative to the second element base, and further defines a deflectable portion having a tip end, wherein the deflectable portion deflects relative to the base portion in the protruding direction upon cooperation with protrusions of the first element, and
   a processor electrically connected with the at least one deflectable transducer to register generated activation signals, and configured to determine, from registered activation signals, an amount of drug delivered or to be delivered from the drug injection device,
   wherein the at least one of the deflectable transducer comprises:
   a carrier foil that extends from the base portion to the tip end of the deflectable portion, and
   a sensor element comprising a strain sensitive material disposed on the carrier foil and extending from the base portion towards the tip end of the deflectable portion, and
   wherein the carrier foil, between the base portion and tip end of the deflectable portion, comprises a non-supported portion having said strain sensitive material disposed at least partly along the non-supported portion.

2. The drug injection device as defined in claim 1, wherein at least the non-supported portion of the carrier foil includes portions having a thickness in the protruding direction of within 40-500 microns.

3. The drug injection device as defined in claim 2, wherein at least the non-supported portion of the carrier foil includes portions having a thickness in the protruding direction of within 50-250 microns.

4. The drug injection device as defined in claim 2, wherein at least the non-supported portion of the carrier foil includes portions having a thickness in the protruding direction of within 75-200 microns.

5. The drug injection device as defined in claim 2, wherein at least the non-supported portion of the carrier foil includes portions having a thickness in the protruding direction of within 100-125 microns.

6. The drug injection device as defined in claim 1, wherein the deflectable portion of the at least one deflectable transducer is configured to sequentially cooperate with the protrusions of the first element by directly engaging the protrusions of the first element.

7. The drug injection device as defined in claim 1, wherein said relative movement is provided as a unidirectional movement of the first element relative to the second element in a first direction, wherein the carrier foil for a respective deflectable transducer is arranged so that it comprises a first segment extending from the base portion generally counter to the first direction to a bending portion, and further comprises a second segment extending in a direction generally in the first direction from the bending portion to the tip end of the deflectable portion so that the second segment includes sub-segments that form angles less than 80 degrees relative to the first sub-portion, and wherein the non-supported portion of the carrier foil having said strain sensitive material disposed is arranged along the second segment.

8. The drug injection device as defined in claim 7, wherein the strain sensitive material is disposed at portions including the bending portion of the carrier foil on the radially inwards facing surface thereof.

9. The drug injection device as defined in claim 7, wherein the second segment extending in a direction generally in the first direction from the bending portion to the tip end of the deflectable portion so that the second segment includes sub-segments that form angles less than 60 degrees relative to the first sub-portion, and wherein the non-supported portion of the carrier foil having said strain sensitive material disposed is arranged along the second segment.

10. The drug injection device as defined in claim 7, wherein the second segment extending in a direction generally in the first direction from the bending portion to the tip end of the deflectable portion so that the second segment includes sub-segments that form angles less than 40 degrees relative to the first sub-portion, and wherein the non-supported portion of the carrier foil having said strain sensitive material disposed is arranged along the second segment.

11. The drug injection device as defined in claim 1, wherein, for each one of the at least one deflectable transducer, the deflectable transducer sequentially cooperates with the protrusions of the first element by cooperating indirectly via a respective activation arm arranged between the first element and the deflectable transducer, wherein the activation arm comprises a base fixedly arranged relative to the second element and a deflectable end being configured to resiliently deflect in the protruding direction upon cooperation with the protrusions of the first element, and wherein the deflectable end of the carrier foil cooperates with the deflectable end of the activation arm by direct engagement with the activation arm.

12. The drug injection device as defined in claim 11, wherein the deflectable portion of the carrier foil is not attached to the deflectable end of the activation arm.

13. The drug injection device as defined in claim 11, wherein a retaining element is arranged to retain the base portion of the at least one deflectable transducer relative to the second element base, the base portion of the at least one deflectable transducer being clamped between the retaining element and the second element base.

14. The drug injection device as defined in claim 13, wherein the retaining element comprises a retaining portion configured to provide a spring force onto the base portion of the deflectable transducer for urging the base portion into contact with the second element base.

15. The drug injection device as defined in claim 1, wherein said relative movement is a relative rotational movement around an axis, wherein the first element defines a cylindrical member arranged coaxially with the axis and wherein the protrusions are regularly disposed on the first element around the axis.

16. The drug injection device as defined claim 1, wherein the drug injection device defines a ratchet mechanism between the first element and the second element so as to prevent relative movement between the first element and the second element in a direction counter to said relative movement.

17. The drug injection device as defined in claim 1, wherein the at least one deflectable transducer is provided as, or comprises, one of a piezoelectric sensor, a piezoresistive sensor and a strain gauge.

18. The drug injection device as defined in claim 1, wherein the at least one of the deflectable transducer comprise piezoelectric material formed onto the carrier foil by a printing process.

19. The drug injection device as defined claim 1, wherein the carrier foil defines a carrier foil sheet, wherein at least one deflectable transducer is provided as a plurality of deflectable transducers that are formed on the carrier foil sheet, the carrier foil sheet being common to the plurality of deflectable transducers, and wherein the processor is disposed on said carrier foil sheet.

20. The drug injection device as defined in claim 1, wherein the drug injection device defines a housing extending along a longitudinal axis, and further comprises a drug expelling mechanism configured to expel a volume of drug from a reservoir, wherein the first element and/or the second element form part of the drug expelling mechanism, and wherein said relative movement is provided as a relative unidirectional movement between the first element and the second element about the longitudinal axis during a drug expelling action in accordance with an expelled dose.

* * * * *